(12) United States Patent
Damen

(10) Patent No.: US 7,676,332 B2
(45) Date of Patent: Mar. 9, 2010

(54) SYSTEM AND METHOD FOR PROCESSING RAW ACTIVITY ENERGY EXPENDITURE DATA

(75) Inventor: Erik Petrus Nicolaas Damen, Doorwerth (NL)

(73) Assignee: Kersh Risk Management, Inc., Plano, TX (US)

( * ) Notice: Subject to any disclaimer, the term of this patent is extended or adjusted under 35 U.S.C. 154(b) by 34 days.

(21) Appl. No.: 11/965,238

(22) Filed: Dec. 27, 2007

(65) Prior Publication Data
US 2009/0171614 A1  Jul. 2, 2009

(51) Int. Cl.
*G01L 5/14* (2006.01)
*G01P 15/00* (2006.01)

(52) U.S. Cl. .................. 702/44; 600/300; 702/141; 702/182

(58) Field of Classification Search .......... 702/44, 702/141, 142, 144, 160, 176, 182; 600/300, 600/549; 482/1, 8; 709/223
See application file for complete search history.

(56) References Cited

U.S. PATENT DOCUMENTS

| | | | |
|---|---|---|---|
| 4,101,071 A | 7/1978 | Brejnik et al. |
| 4,855,942 A | 8/1989 | Bianco |
| 4,911,427 A | 3/1990 | Matsumoto et al. |
| 4,951,197 A | 8/1990 | Mellinger |
| 4,962,469 A | 10/1990 | Ono et al. |
| 5,108,989 A | 4/1992 | Amento et al. |
| 5,117,444 A | 5/1992 | Sutton et al. |
| 5,410,472 A | 4/1995 | Anderson |
| 5,436,228 A | 7/1995 | Postlethwaite et al. |
| 5,466,200 A | 11/1995 | Ulrich et al. |
| 5,474,090 A | 12/1995 | Begun et al. |
| 5,527,239 A | 6/1996 | Abbondanza |
| 5,573,013 A | 11/1996 | Conlan |
| 5,593,431 A | 1/1997 | Sheldon |
| 5,598,849 A | 2/1997 | Browne |
| 5,611,806 A | 3/1997 | Jang |

(Continued)

FOREIGN PATENT DOCUMENTS

DE  195 18 932 A1  11/1995

(Continued)

OTHER PUBLICATIONS

Diabetech, "News at Diabetech," http://www.diabetech.net, Aug. 27, 2004, 8 pages.

(Continued)

*Primary Examiner*—John H Le
(74) *Attorney, Agent, or Firm*—Patent Capital Group

(57) ABSTRACT

According to one embodiment, a method is provided for calculating, by an activity monitor comprising one accelerometer, a raw activity energy expenditure data based on movement by a user. The method includes determining if the raw activity energy expenditure data is associated with a high intensity physical activity, wherein the high intensity physical activity causes the raw activity energy expenditure data to differ from an expected activity energy expenditure data. The method includes calculating a corrected activity energy expenditure data, if the raw activity energy expenditure data is associated with the high intensity physical activity, based on the raw activity energy expenditure data, wherein the corrected activity energy expenditure data is substantially identical to the expected activity energy expenditure data.

27 Claims, 6 Drawing Sheets

U.S. PATENT DOCUMENTS

| | | | |
|---|---|---|---|
| 5,649,968 A | 7/1997 | Alt et al. |
| 5,702,323 A | 12/1997 | Poulton |
| 5,749,372 A | 5/1998 | Allen et al. |
| 5,785,978 A | 7/1998 | Porter et al. |
| 5,788,655 A | 8/1998 | Yoshimura et al. |
| 5,807,283 A | 9/1998 | Ng |
| 5,810,747 A | 9/1998 | Brudny et al. |
| 5,813,863 A | 9/1998 | Sloane et al. |
| 5,885,231 A | 3/1999 | Cramer et al. |
| 5,890,997 A | 4/1999 | Roth |
| 5,899,963 A | 5/1999 | Hutchings |
| 5,916,063 A | 6/1999 | Alessandri |
| 5,919,149 A | 7/1999 | Allum |
| 5,925,001 A | 7/1999 | Hoyt et al. |
| 5,931,763 A | 8/1999 | Alessandri |
| 5,955,667 A | 9/1999 | Fyfe |
| 5,964,729 A | 10/1999 | Choi et al. |
| 5,967,789 A | 10/1999 | Segel et al. |
| 5,973,618 A | 10/1999 | Ellis |
| 5,976,083 A | 11/1999 | Richardson et al. |
| 5,989,200 A | 11/1999 | Yoshimura et al. |
| 6,021,351 A | 2/2000 | Kadhiresan et al. |
| 6,030,404 A | 2/2000 | Lawson et al. |
| 6,032,530 A | 3/2000 | Hock |
| 6,039,688 A | 3/2000 | Douglas et al. |
| 6,045,513 A | 4/2000 | Stone et al. |
| 6,046,761 A | 4/2000 | Echerer |
| 6,052,654 A | 4/2000 | Gaudet et al. |
| 6,063,046 A | 5/2000 | Allum |
| 6,065,138 A | 5/2000 | Gould et al. |
| 6,080,106 A | 6/2000 | Lloyd et al. |
| 6,095,991 A | 8/2000 | Krausman et al. |
| 6,101,478 A | 8/2000 | Brown |
| 6,122,340 A | 9/2000 | Darley et al. |
| 6,135,951 A | 10/2000 | Richardson et al. |
| 6,145,389 A | 11/2000 | Ebeling et al. |
| 6,151,586 A | 11/2000 | Brown |
| 6,168,569 B1 | 1/2001 | McEwen et al. |
| 6,206,829 B1 | 3/2001 | Lliff |
| 6,229,454 B1 | 5/2001 | Heikkila et al. |
| 6,240,393 B1 | 5/2001 | Brown |
| 6,273,856 B1 | 8/2001 | Sun et al. |
| 6,290,646 B1 | 9/2001 | Cosentino et al. |
| 6,305,221 B1 | 10/2001 | Hutchings |
| 6,356,856 B1 | 3/2002 | Damen et al. |
| 6,377,179 B1 | 4/2002 | Fulton |
| 6,454,705 B1 | 9/2002 | Cosentino et al. |
| 6,473,483 B2 | 10/2002 | Pyles |
| 6,478,736 B1 | 11/2002 | Mault |
| 6,497,638 B1 | 12/2002 | Shea |
| 6,506,152 B1 | 1/2003 | Lackey et al. |
| 6,513,532 B2 | 2/2003 | Mault et al. |
| 6,516,749 B1 | 2/2003 | Salasidis |
| 6,519,495 B1 | 2/2003 | Sun et al. |
| 6,571,200 B1 | 5/2003 | Mault |
| 6,578,291 B2 | 6/2003 | Hirsch et al. |
| 6,582,380 B2 | 6/2003 | Kazlausky et al. |
| 6,590,536 B1 | 7/2003 | Walton |
| 6,604,419 B2 | 8/2003 | Guzman |
| 6,605,038 B1 | 8/2003 | Teller et al. |
| 6,605,044 B2 | 8/2003 | Bimbaum |
| 6,626,799 B2 | 9/2003 | Watterson et al. |
| 6,669,600 B2 | 12/2003 | Warner |
| 6,692,436 B1 | 2/2004 | Bluth et al. |
| 6,703,939 B2 | 3/2004 | Lehrman et al. |
| 6,714,133 B2 | 3/2004 | Hum et al. |
| 6,731,213 B1 | 5/2004 | Smith |
| 6,790,178 B1 | 9/2004 | Mault |
| 6,805,006 B2 | 10/2004 | Guzman |
| 6,807,869 B2 | 10/2004 | Farringdon et al. |
| 6,819,247 B2 | 11/2004 | Birnbach et al. |
| 6,825,777 B2 | 11/2004 | Vock et al. |
| 6,878,121 B2 | 4/2005 | Krausman et al. |
| 6,898,550 B1 * | 5/2005 | Blackadar et al. ........... 702/182 |
| 6,918,858 B2 | 7/2005 | Watterson et al. |
| 6,928,324 B2 | 8/2005 | Park et al. |
| 6,997,852 B2 | 2/2006 | Watterson et al. |
| 6,997,882 B1 | 2/2006 | Parker et al. |
| 7,108,681 B2 | 9/2006 | Gartstein et al. |
| 7,137,566 B2 | 11/2006 | Silverbrook et al. |
| 7,156,289 B2 | 1/2007 | Silverbrook et al. |
| 7,178,718 B2 | 2/2007 | Silverbrook et al. |
| 7,181,488 B2 | 2/2007 | Silverbrook et al. |
| 7,184,962 B2 | 2/2007 | Kalnas et al. |
| 7,278,966 B2 | 10/2007 | Hjelt et al. |
| 7,373,820 B1 | 5/2008 | James |
| 7,502,255 B2 | 3/2009 | Li |
| 7,559,877 B2 | 7/2009 | Parks et al. |
| 7,603,255 B2 | 10/2009 | Case et al. |
| 2001/0004234 A1 | 6/2001 | Petelenz et al. |
| 2001/0047125 A1 | 11/2001 | Quy |
| 2001/0048364 A1 | 12/2001 | Kalthoff et al. |
| 2002/0013717 A1 | 1/2002 | Ando et al. |
| 2002/0082906 A1 | 6/2002 | Kirshner |
| 2002/0099356 A1 | 7/2002 | Unger et al. |
| 2002/0109600 A1 | 8/2002 | Mault et al. |
| 2003/0017848 A1 | 1/2003 | Engstrom et al. |
| 2003/0050537 A1 | 3/2003 | Wessel |
| 2003/0122677 A1 | 7/2003 | Kail |
| 2003/0126593 A1 | 7/2003 | Mault |
| 2003/0135391 A1 | 7/2003 | Edmundson et al. |
| 2003/0199811 A1 | 10/2003 | Sage et al. |
| 2003/0208110 A1 | 11/2003 | Mault et al. |
| 2004/0049251 A1 | 3/2004 | Knowlton |
| 2004/0052750 A1 | 3/2004 | Lee et al. |
| 2004/0087992 A1 | 5/2004 | Gartstein et al. |
| 2004/0092367 A1 | 5/2004 | Corbalis et al. |
| 2004/0111291 A1 | 6/2004 | Dust et al. |
| 2004/0130446 A1 | 7/2004 | Chen et al. |
| 2004/0132461 A1 | 7/2004 | Duncan |
| 2004/0133455 A1 | 7/2004 | McMahon |
| 2004/0247748 A1 | 12/2004 | Bronkema |
| 2004/0249315 A1 | 12/2004 | Damen |
| 2004/0260210 A1 | 12/2004 | Ella et al. |
| 2005/0010439 A1 | 1/2005 | Short |
| 2005/0107723 A1 | 5/2005 | Wehman et al. |
| 2005/0137531 A1 | 6/2005 | Prausnitz et al. |
| 2005/0202934 A1 | 9/2005 | Olrik et al. |
| 2005/0209061 A1 | 9/2005 | Crawford et al. |
| 2005/0225868 A1 | 10/2005 | Nelson et al. |
| 2005/0228692 A1 | 10/2005 | Hodgdon |
| 2005/0234742 A1 | 10/2005 | Hodgdon |
| 2005/0245793 A1 | 11/2005 | Hilton et al. |
| 2006/0025282 A1 | 2/2006 | Redmann |
| 2006/0229163 A1 | 10/2006 | Waters |
| 2006/0264730 A1 | 11/2006 | Stivoric et al. |
| 2007/0073217 A1 | 3/2007 | James |
| 2007/0135264 A1 | 6/2007 | Rosenberg |
| 2007/0135690 A1 | 6/2007 | Nicholl |
| 2007/0219059 A1 | 9/2007 | Schwartz et al. |
| 2007/0260483 A1 | 11/2007 | Nurmela et al. |
| 2008/0086325 A1 | 4/2008 | James |
| 2008/0090703 A1 | 4/2008 | Rosenberg |
| 2008/0096726 A1 | 4/2008 | Riley et al. |
| 2008/0155077 A1 | 6/2008 | James et al. |
| 2008/0176655 A1 | 7/2008 | James |
| 2008/0182723 A1 | 7/2008 | Aaron et al. |
| 2008/0258921 A1 | 10/2008 | Woo et al. |
| 2008/0306762 A1 | 12/2008 | James |
| 2008/0306763 A1 | 12/2008 | James |
| 2009/0005220 A1 | 1/2009 | Lee et al. |
| 2009/0048493 A1 | 2/2009 | James et al. |
| 2009/0093341 A1 | 4/2009 | James et al. |
| 2009/0204422 A1 | 8/2009 | James |

| | | |
|---|---|---|
| 2009/0216629 A1 | 8/2009 | James |

FOREIGN PATENT DOCUMENTS

| | | |
|---|---|---|
| EP | 0797 169 A1 | 9/1997 |
| EP | 1 159 989 A1 | 12/2001 |
| EP | 1 366 712 | 12/2003 |
| WO | WO 96/29007 | 9/1996 |
| WO | WO 00/52604 | 9/2000 |
| WO | WO 02/069803 | 9/2002 |
| WO | WO 02/091923 A1 | 11/2002 |
| WO | WO 03/089069 A1 | 10/2003 |
| WO | WO 2007/011788 | 1/2007 |

OTHER PUBLICATIONS

Horst Liebl, Co., "Confidential—Evaluation II—On the Needling-device Medical Roll-CIT," made by Environ, May 2001, 5 pages.

K. Anastassakis, M.D., Ph.D., "The Dermaroller Series," May 2005, 28 pages.

D.R. Owen, Ph.D., "Peptides, Oligopeptides, Lipopeptides and Polypeptides," Official Publication of the Society of Plastic Surgical Skin Care Specialists, Spring 2005, 2 pages.

"History of the Dermaroller," www.dermaroller.de/History.htm, printed approximately Jul. 2005, 7 pages.

DermaRoller™, http://www.dermaroller.de/derma_engl.htm, printed Jul. 11, 2005, 4 pages.

"The Dermaroller—A New and Highly Effective Procedure to Treat Acne-Scars by Micro-Needling," approx. 2005, 3 pages.

Horst Liebl, Co., "The Collagen-Induction-Therapy CIT with the CIT-Roller," approx. 2005, 3 pages.

DermaRolleCr™-Models, approx. 2005, 3 pages.

"The Dermaroller—An Effective Alternative for Scar-Therapies," approx. 2005, 5 pages.

"The Collagen-Induction-Therapy (CIT) with the DermaRoller™-The "soft" alternative for all common Laser & Peeling-Methods," approx. 2005, 5 pages.

Frequently Asked Questions (FAQs) About the DermarRoller™, approx. 2005, 4 pages.

Horst Liebl, Co., "Technical evaluation of the Roll-CIT," Manufactured by ENVIRON—South Africa, approx. 2005, 3 pages.

Horst Liebl, Co., "Technical Data & Description of the DermaRoller™," approx. 2005, 1 page.

Notification of Transmittal of the International Search Report and the Written Opinion of the International Searching Authority, or the Declaration for International Application No. PCT/US06/27502 mailed Mar. 19, 2007, 6 pages.

Clark, R.A.,"Biology of Dermal Wound Repair," Dermatologic Clinics, Oct. 1993, vol. 11, No. 4, pp. 647-666 (20 pages).

"Sport Brain First Step Pack," sportbrain.com (1 page) downloaded from http://www.sportbrain.com/Home/home.cfm?page=productsb_show&sk=c1235&us=99.95&cod=CL235 on Dec. 19, 2006.

"Nike + ipod Sport Kit," nike.com (1 page) downloaded from http://www.nike.com/index.ihtml#1=nikestore.home._pdp.cid-1/gid-118523/pid-118523&re=US&co=US&Ia=EN on Dec. 19, 2006.

"What is the Bodybugg?," bodybugg.com (2 pages) downloaded from http://www.bodybugg.com/whatis.phpon Dec. 19, 2006.

"BioTrainer Weight Loss System," Biotrainerusa.com (3 pages) downloaded from http://www.biotrainerusa.com/learn2.asp on Dec. 19, 2006.

MSN Encarta—Definition of Accelerometer; date accessed: Nov. 19, 2007; http://encarta.msn.com/dictionary_1861583213/accelerometer.html; 2 pages.

Voicescape Absence Manager website with product description and information at http://absencemanager.voicescape.co.uk/sam/home/index.cfm, May 2008, 1 page.

"MySpace," myspace.com (2 pages) downloaded from http://www.myspace.com/, printed Jan. 16, 2007.

International Search Report for International Application No. PCT/EP02/04968 mailed Oct. 10, 2002, 3 pages.

Notification of Transmittal of the International Preliminary Examination Report and International Preliminary Examination Report for International Application No. PCT/EP02/04968 mailed Jul. 8, 2003, 12 pages.

U.S. Appl. No. 10/819,730, filed Apr. 7, 2004, entitled "System and Method for Measuring an Economic Efficacy of an Intervention," Inventor(s) Richard W. Kersh, et al.

U.S. Appl. No. 10/915,916, filed Aug. 11, 2004, entitled "Process, System, and Method for Managing Healthcare Expenditures," Inventor(s) Terry L. James.

Raitio, Maarit. Caries risk determination and cost-effectiveness of targeted prevention in adolescents. Oulun yliopisto. Oulun University Library. 2002. Chapter 6.6. (3 pages) Printed Jun. 27, 2008 from http://Herkules.oulu.fi/ . . . .

U.S. Appl. No. 10/915,851, filed Aug. 11, 2004, entitled "System and Method for Designing an Intervention," Inventor(s) Terry L. James.

Jason, Leonard A., et al. Incentives and Competition in a Worksite Smoking Cessation Intervention. American Journal of Public Health. Feb. 1990. vol. 80, No. 2, p. 205 (3 pages).

Gaynor, Martin, et al. Physician Incentives in Health Maintenance Organizations. The Journal of Political Economy. Chicago: Aug. 2004. vol. 112, Iss. 4; p. 915 (17 pages).

U.S. Appl. No. 10/916,579, filed Aug. 11, 2004, entitled "System and Method for Implementing an Incentive Program to Encourage Participation in an Intervention," Inventor(s) Terry L. James.

U.S. Appl. No. 10/915,582, filed Aug. 11, 2004, entitled "System and Method for Population Health Management Data Collection and Communication," Inventor(s) Terry L. James.

"SportBrain Personal Fitness Assistant," sportbrain.com (1 page) downloaded from http://www.sportbrain.com/Home/Home.cfm, Jan. 16, 2007.

"NikePlus," nike.com (1 page) downloaded from http://www.nike.com/nikeplus, Jan. 16, 2007.

"Bodybugg Customized Calorie Management," bodybugg.com (2 pages) downloaded from http://www.bodybugg.com/fitness_resources.php, Jan. 16, 2007.

"BioTrainer Monitoring Programs," biotrainerusa.com (2 pages) downloaded from http://www.biotrainerusa.com/monitoring.asp, Jan. 16, 2007.

U.S. Appl. No. 12/098,539, filed Apr. 7, 2008, entitled "Accelerometer for Data Collection and Communication," Inventor(s): Terry L. James.

U.S. Appl. No. 12/176,369, filed Jul. 19, 2008, entitled "System and Method for Monitoring, Measuring, and Addressing Stress," Inventor(s): Terry L. James.

\* cited by examiner

SYSTEM AND METHOD FOR PROCESSING RAW ACTIVITY ENERGY EXPENDITURE DATA

TECHNICAL FIELD OF THE INVENTION

This invention relates in general to an activity monitor and, more particularly, to a system and a method for processing raw activity energy expenditure data.

BACKGROUND OF THE INVENTION

An activity monitor allows the measurement of human energy expenditure. The activity monitor allows the user wearing the activity monitor to measure the amount of energy consumed during a selected period of time for a certain physical activity, such as walking and running. An activity monitor utilizing a single accelerometer is less expensive and consumes less power than an activity monitor utilizing a plurality of accelerometers. A single accelerometer may be a uni-axial accelerometer that generates a signal, which is proportional to the energy expenditure, such that the signal is generated in response to body movements in the particular direction along the single axis of the accelerometer.

When user is performing a low intensity physical activity, such as walking, the dominant direction of body movement is the up and down direction occurring along the vertical axis. If the accelerometer is properly aligned with the body movement of user to measure movements along the vertical axis, the activity monitor will provide a signal, which is a relatively accurate representation of the energy expenditure by the user. However, when user is performing a high intensity physical activity, such as running, the forward and backward movement of the body provides an additional, non-negligible contribution to energy expended by the user. In response to the backward and forward movement occurring along the horizontal axis during high intensity physical activity, the accelerometer will provide a signal, which is an inaccurate representation of the actual energy expenditure by the user because the accelerometer primarily measures movements along the vertical axis. Therefore, the energy expenditure measured by the uni-axial accelerometer in the activity monitor will deviate from the real energy expenditure of the user. One way to solve this problem for accurately measuring energy expended requires using an additional accelerometer, which can measure forward and backward body movement along the horizontal axis. However, this additional sensor will increase the cost of the activity monitor, and the amount of power consumed by the activity monitor.

Additionally, an activity monitor with only one sensor, such as a uni-axial accelerometer, does not include hardware operable to calculate the speed of a user while the user is walking or running. One way to solve this problem for determining the speed of the user requires using an additional sensor for tracking speed, such as an accelerometer worn on the foot or shoe, a switch on the sole of the shoe, or a GPS sensor. However, this additional sensor will increase the cost of the activity monitor, and the amount of power consumed by the activity monitor.

SUMMARY OF THE INVENTION

In accordance with the present invention, a method, a system, and an apparatus for collecting, converting, displaying, and communicating data is provided, which substantially eliminates or reduces the disadvantages and problems associated with previous systems, methods, and apparatuses.

According to one embodiment, a method is provided for calculating, by an activity monitor comprising one accelerometer, a raw activity energy expenditure data based on movement by a user. The method includes determining if the raw activity energy expenditure data is associated with a high intensity physical activity, wherein the high intensity physical activity causes the raw activity energy expenditure data to differ from an expected activity energy expenditure data. The method includes calculating a corrected activity energy expenditure data, if the raw activity energy expenditure data is associated with the high intensity physical activity, based on the raw activity energy expenditure data, wherein the corrected activity energy expenditure data is substantially identical to the expected activity energy expenditure data. The method may display the corrected activity energy expenditure data the corrected activity energy expenditure data in METs is calculated by $(RawAEE\_MET-T)*B+F$, wherein RawAEE MET is the raw activity energy expenditure data, wherein T is a predetermined threshold value associated with the high intensity physical activity, wherein B is a predetermined gradient value, wherein F is a predetermined offset value.

According to one embodiment, a method is provided for determining a speed of the user based on the corrected activity energy expenditure data and displaying the speed of the user. The speed of the user may be determined by $(CorAEE\_MET-1)/G$, wherein CorAEE_MET is the corrected activity energy expenditure data in metabolic equivalents (METs), wherein 1 is one MET, wherein G is a predetermined gradient value of 0.95 hours/kilometers (h/km) during high intensity physical activity, such as running, or 0.49 h/km during light intensity physical activity, such as walking.

Important technical advantages of certain embodiments of the present invention include utilizing a single uni-axial accelerometer to accurately calculate activity energy expended by user during both low intensity and high intensity activities. As a result of only requiring a single accelerometer to accurately measure activity energy expended by user, the activity monitor is less expensive and consumes less power than activity monitors with additional sensors for accomplishing this task.

Other technical advantages of certain embodiments of the present invention include utilizing a single uni-axial accelerometer to calculate speed of user during both low intensity and high intensity activities. As a result of only requiring a single accelerometer to accurately measure speed of user, activity monitor is less expensive and consumes less power than an activity monitor with additional sensors for accomplishing this task. Prior solutions may utilize the global position system (GPS), but the GPS requires high-energy consumption of activity monitor, which requires the user to frequently charge or replace batteries used by activity monitor.

Other technical advantages of certain embodiments of the present invention include utilizing a single uni-axial accelerometer to obtain continuous display of speed and distance without requiring a sensor attached to the user's foot. Prior solutions included attaching one or more sensors to the foot or shoe of the user, such that the sensors monitor the acceleration of the foot. The data may be single or double integrated to obtain speed and distance information of the step. The sensors may monitor the time the foot is on the ground compared to in the air, from which an estimate can be made of walking or running speed. One advantage of the present invention is that no special attachment to the shoe is necessary to obtain continuous read-out of speed and distance.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which.

DETAILED DESCRIPTION OF EXAMPLE EMBODIMENTS

Figure 1:
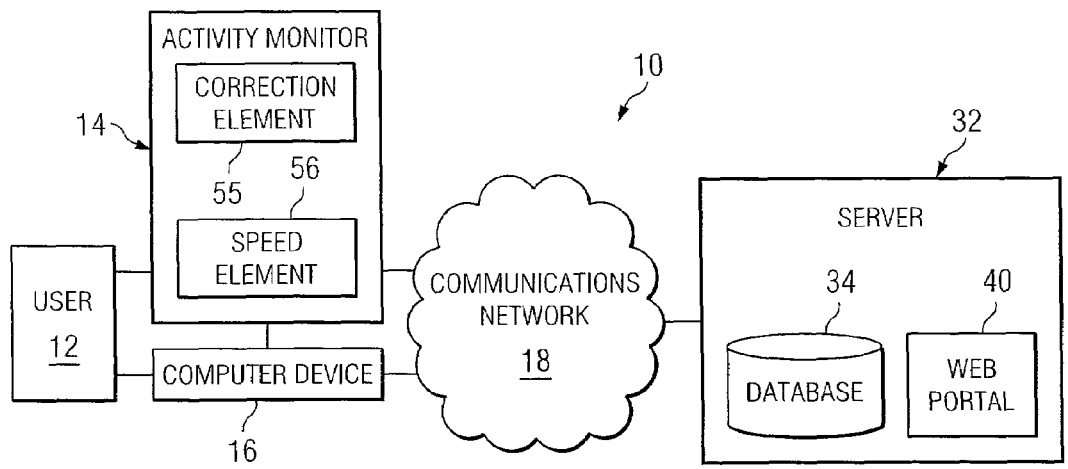
FIG. 1 is a simplified block diagram that illustrates a system in accordance with a particular embodiment of the present invention.

FIG. 1 is a simplified block diagram that illustrates a system in accordance with a particular embodiment of the present invention. System 10 includes a communication network 18, a user 12, one or more computer devices 16, an activity monitor 14, one or more servers 32, one or more databases 34, and a web portal 40. Activity monitor 14 may include a correction element 55 and a speed element 56. Other architectures and components of system 10, including various architectures and components of activity monitor 14, may be used without departing from the scope of this disclosure.

In general, users 12 may wear an activity monitor 14 to track one or more activity data metrics associated with an activity. Activity data may include the calories burned, metabolic equivalents (METs) expended, physical activity monitor (PAM) points spent (where PAM points may be defined as activity induced energy expenditure divided by the basal metabolic rate multiplied by 100), minutes in light activity zone, minutes in medium activity zone, minutes in high activity zone, current speed, distance traveled, etcetera. Users 12 may couple activity monitor 14 to one or more computer devices 16, which provide users access to a web portal 40. Activity monitor 14 may transmit data to web portal 40. Web portal 40 may utilize activity data to provide user 12 with feedback or goals in response to the activity data.

In one particular embodiment, activity monitor 14 may use calories as the activity data metric to calculate the raw activity energy expenditure data (RawAEE) by user 12. In this embodiment, the equation used by activity monitor 14 for determining the raw calories expended by user 12 may be:

$$Raw AEE\_Cal = (c * |a|) * BMR$$

The variable $|a|$ used by RawAEE_Cal is a value determined by activity monitor 14 based on signals generated by accelerometer in response to activity by user 12. The variable $|a|$ may refer to the average of the absolute value of acceleration data over a particular time period. Determining the value of $|a|$ is explained in more detail below in FIG. 3. The constants, c and BMR, used by RawAEE_Cal may be a predetermined value stored in activity monitor 14. These predetermined values associated with the constants may be stored in activity monitor 14 during the manufacture process of activity monitor 14, by downloading new software for activity monitor 14, or any other suitable way. The constant c may be a predetermined value used to multiply against $|a|$ to produce an expected value. The constant BMR refers to the basal metabolic rate. The BMR is the amount of energy, such as calories, that user 12 consumes at rest.

In one particular embodiment, activity monitor 14 may use METs as the activity data metric to calculate the raw activity energy expenditure data (RawAEE_MET) by user 12. In this embodiment, the equation used by activity monitor 14 for determining the raw METs expended by user 12 may be:

$$Raw AEE\_MET = (c * |a|) + 1$$

The variable $|a|$ used by RawAEE_MET is a value determined by activity monitor 14 based on signals generated by accelerometer in response to activity by user 12. The variable $|a|$ may refer to the average of the absolute value of acceleration data over a particular time period. Determining the value of $|a|$ is explained in more detail below in FIG. 3. The constants, c and 1, used by RawAEE_MET may be a predetermined value stored in activity monitor 14. These predetermined values associated with the constants may be stored in activity monitor 14 during the manufacture process of activity monitor 14, by downloading new software for activity monitor 14, or any other suitable way. The constant c may be a predetermined value used to multiply against $|a|$ to produce an expected value. For example, the constant c may be a value determined by the amplification factor of the amplifier electronics of activity monitor 14 in addition to the type of analog to digital converter used by activity monitor 14. The constant 1 refers to one MET.

In one particular embodiment, activity monitor 14 may use PAM points as the activity data metric to calculate the raw activity energy expenditure data (RawAEE_PAM) by user 12. In this embodiment, the equation used by activity monitor 14 for determining the raw PAM points expended by user 12 may be:

$$Raw AEE\_PAM = c * |a|$$

The variable $|a|$ used by RawAEE_PAM is a value determined by activity monitor 14 based on signals generated by accelerometer in response to activity by user 12. The variable $|a|$ may refer to the average of the absolute value of acceleration data over a particular time period. Determining the value of $|a|$ is explained in more detail below in FIG. 3. The constant c used by RawAEE_PAM may be a predetermined value stored in activity monitor 14. These predetermined values associated with the constants may be stored in activity monitor 14 during the manufacture process of activity monitor 14, by downloading new software for activity monitor 14, or any other suitable way. The constant c may be a predetermined value used to multiply against |a| to produce an expected value. In alternative embodiments, PAM points may be defined differently such that RawAEE_PAM may utilize a different equation for determining the raw PAM points expended by user 12. Additionally, other alternative embodiments may utilize other activity data metrics for determining the raw activity data of energy expended by user 12.

It is important to mention that activity monitor 14 is operable to determine the energy expended for one or more activity data metrics without requiring user 12 to enter any personal information. For example, METs and PAM points are substantially independent of body weight. Therefore, METs and PAM points can express activity energy expended by user 12 without knowledge of user's personal information, such as gender, age, height, or weight. As a result, activity monitor 14 may be operable to provide activity data in METs and PAM points without requiring user 12 to input any personal information. Activity monitor 14 may store the necessary equations and data for calculating the energy expended in activity monitor 14 during the manufacture process of activity monitor 14, by downloading new software for activity monitor 14, or any other suitable way.

It is also important to mention that activity monitor 14 is operable to determine the speed of user 12 without requiring user 12 to enter any personal information. User's speed may be a direct relationship to the METs or PAM points expended by user 12. Activity monitor 14 may store the necessary equations and data for determining the speed of user in activity monitor 14 during the manufacture process of activity monitor 14, by downloading new software for activity monitor 14, or any other suitable way. The speed element 56 calculates the speed of user 12, and this is discussed in more detail below.

In one embodiment, activity monitor 14 may also measure the time spent by user 12 in the light, medium, and high activity zones. Literature or information available on web portal 40 may instruct users 12 how much time should be spent in each activity zone. The light activity zone may be associated with energy expended by user 12 while fidgeting, i.e., not a sedentary state, but also not walking at a brisk pace or activity with similar intensity. For example, data indicating speed of less than four kilometers per hour (km/h) but more than one km/h or activity energy expended data representing more than two METs but less than four METs may be associated with the light activity zone. The medium activity zone may be associated with energy expended by user 12 during low intensity physical activity, such as walking. For example, data indicating speed greater than four km/h and less than eight km/h or activity energy expended data greater than three METs and less than seven METs may be associated with the medium activity zone. The high activity zone may be associated with energy expended by user during high intensity physical activity, such as running. For example, data indicating speed of greater than eight km/h or activity energy expended data greater than seven METs may be associated with the high activity zone. The light activity zone may be referred to as the life activity zone, the medium activity zone may be referred to as the health activity zone, and the high activity zone may be referred to as the sports zone. In alternative embodiments, the activity zones may utilize different threshold values. In another embodiment, the activity zones may utilize different activity data metrics, such as PAM points.

In accordance with the teachings of the present invention, system 10 achieves an effective way for activity monitor 14 to correct raw activity energy expended data when user 12 is engaged in high intensity physical activity, such as running. System 10 also achieves an effective way for activity monitor 14 to determine the speed of user 12 based on the corrected activity energy expended data. Activity monitor 14 comprising a single accelerometer may produce signals proportional to energy expenditure of user 12. The single accelerometer may produce signals associated with the up and down (vertical) axis, such that signals are generated in response to user's body movement in the up and down (vertical) axis.

During physical activities requiring low intensity, such as walking, activity monitor 14 may process these signals to a raw activity data metric, such that this activity data metric may represent an accurate value of the actual energy expended by user 12. This raw activity energy expended data may be accurate while user 12 is walking because the dominant direction of user's body movement is in the up and down direction occurring along the vertical axis. However, during physical activities requiring high intensity, such as running, activity monitor 14 may process these signals to a raw activity energy expended data metric, such that this raw activity energy expended data may represent an inaccurate value of the actual energy expended by user 12. This raw activity energy expended data may be inaccurate because user 12 expends additional energy with forward and backward (horizontal) movement of user's body during high intensity activity, such as running.

The single accelerometer associated with recording movement along the vertical axis may not be able to produce accurate signals associated with user's body movement in the backward and forward direction occurring along the horizontal axis. Correction element 55 may receive the raw activity energy expended data and, if needed, convert the raw activity energy expended data to a corrected activity energy expended data, such that the corrected activity energy expended data represents an accurate value of the actual energy expended by user 12. This corrected activity energy expended data includes energy expended by user 12 in both the horizontal axis and the vertical axis.

Speed element 56 may receive the corrected activity energy expended data to determine the speed of user 12 during high intensity activity. Speed element 56 may use the raw activity energy expended data to determine speed of user 12 during low intensity activity. As a result, activity monitor 14 comprising a single accelerometer may be operable to display the accurate activity energy expended data and the accurate speed of user 12 during both low and high intensity physical activity.

Communication network 18 couples and facilitates wireless or wire line communication between computer devices 16, activity monitors 14, and servers 32. Communication network 18 may, for example, communicate Internet Protocol (IP) packets, Frame Relay frames, Asynchronous Transfer Mode (ATM) cells, voice, video, data, and other suitable information between network addresses. Communication network 18 may also communicate data via wireless communications, such as by Wireless Application Protocol (WAP) standard protocols, including 802.11, third-generation (3G) protocols (such as W-CDMA or CDMA 2000, for example), Bluetooth, or Global System for Mobile Communications (GSM) protocols, for example. Communication network 18 may include one or more local area networks (LANs), radio access networks (RANs), metropolitan area networks (MANs), wide area networks (WANs), interactive television networks, all or a portion of the global computer network known as the Internet, and/or any other communication system or systems at one or more locations.

User 12 may include any individual desiring to use activity monitor 14. User 12 may wear activity monitor 14 and couple activity monitor 14 to one or more computer devices 16 to connect to web portal 40. Users 12 may engage in sedentary activity, low intensity activity, or high intensity activity while wearing activity monitor. User 12 may wear activity monitor 14 for an entire day or only for an event for a specified period of time. In one particular embodiment, users 12 may include physical education students who couple their activity monitors 14 to computer device 16 to transmit the data from activity monitor 14 to web portal 40. Web Portal 40 allows teachers to view the physical activity data of their students and use this information to grade the students according to the curriculum.

Activity monitor 14 is generally operable to measure body movement of user 12. In one embodiment, activity monitor 14 may also store data, receive data, convert data, display data, and transmit data for a multitude of purposes. In one embodiment, activity monitor 14 may comprise a single accelerometer, such that this single accelerometer may measure the user's up and down movement occurring on the vertical axis. Activity monitor 14 may only utilize one activity data metric or activity monitor may utilize a plurality of activity data metrics.

For example, based on signals associated with user's body movement, activity monitor 14 may measure one or more activity data metrics that may include calories, distances, PAM points, METs, speed, life zone minutes, health zone minutes, or sports zone minutes. Memory in activity monitor 14 may include volatile or non-volatile memory including, without limitation, magnetic media, optical media, random access memory (RAM), read-only memory (ROM), removable media, or any other suitable local or remote memory component. In general, the memory may store various data including activity data metrics, equations and constant values associated with the equations, a user's account information, a user's goals, etcetera. For example, user's account information may include a unique identification number associated with each user 12. Activity monitor 14 may be operable to receive data from web portal 40, computer device 16, machine, or any other device. Activity monitor 14 may further operable to transmit data to web portal 40 or computer device 16. Activity monitor 14 may include a graphics card to display streaming video and data stored in memory. Activity monitor 14 may include a processor to convert signals from accelerometer and utilize equations for performing calculations. For example, activity monitor 14 may utilize equations from correction element 55 and/or speed element 56 to determine the actual energy expended by user and the actual speed of user 12. Activity monitor 14 may be operable to receive software updates from server 32. Additional details of activity monitor 14 are listed below in FIG. 2.

Software and/or hardware may reside in activity monitor 14 in order to achieve the teachings of collecting data, converting data, displaying data, and communicating data of the present invention. However, due to their flexibility, activity monitor 14 may alternatively be equipped with (or include) any suitable component, device, application specific integrated circuit (ASIC), processor, microprocessor, algorithm, read-only memory (ROM) element, random access memory (RAM) element, erasable programmable ROM (EPROM), electrically erasable programmable ROM (EEPROM), field-programmable gate array (FPGA), or any other suitable element or object that is operable to facilitate the operations thereof. Considerable flexibility is provided by the structure of activity monitor 14 in the context of system 10 and, accordingly, it should be construed as such.

Correction element 55 may represent any suitable combination of hardware, software, and/or controlling logic operable to receive raw activity energy expended data and process the raw activity energy expended data to determine the corrected activity energy expended data, such that the corrected activity energy expended data represents the actual energy expended by user 12. As explained above, activity monitor 14 may comprise a single uni-axial accelerometer that calculates raw activity energy expended data while user 12 is engaged in high intensity physical activity, such that this raw activity energy expended data represents an inaccurate amount of energy expended by user 12 since the backward and forward movement occurring on the horizontal axis may not be accurately measured by the uni-axial accelerometer measuring the up and down movement occurring on the vertical axis. Correction element 55 may correct the inaccurate raw activity energy expended data, such that the corrected activity energy expended data represents the actual energy expended by user 12 while engaged in high intensity physical activity. As a result, correction element 55 or any suitable component of activity monitor 14 may determine to only correct the raw activity energy expenditure data if the raw activity energy expenditure data is greater than a predetermined threshold value representing the value when the raw activity energy expenditure data begins to become inaccurate as a result of the high intensity physical activity.

In one embodiment, correction element 55 may utilize an equation to determine the corrected activity energy expenditure data (CorAEE). The equation utilized by correction element 55 may be based on the expected activity energy expenditure data (ExpAEE). The expected activity energy expenditure data for a particular activity data metric may be determined by a formula that expresses a relationship between the actual energy expended during low intensity physical activity, such as walking, and the actual energy expended during high intensity physical activity, such as running. The equation for the expected activity energy expenditure data in METs is illustrated below in FIG. 4A.

For example, the equation for calculating the expected activity energy expenditure data using the MET as the physical activity metric may be a function of low intensity physical activity, such as walking, and a function of high intensity physical activity, such as running, as published by the American College of Sports Medicine (Ainsworth et al., Compendium of physical activities: An update of activity codes and MET intensities, Med. Sci. Sports. Exerc. 2000, S498-S516). This equation for calculating the expected activity energy expenditure data in METs may be:

$$\text{Exp}AEE\_\text{MET} = (G^* v) + 1$$

The variable v used to calculate ExpAEE_MET is the velocity of user 12 in terms of km/h. The constant G is 0.49 h/km for low intensity physical activity, such as walking, that occurs while the velocity of user 12 is less than eight km/h. The constant G is 0.95 h/km for high intensity physical activity, such as running, that occurs while the velocity of user 12 is greater than eight km/h. The constant G represents the gradient, such that activity energy expended increases at a gradient of 0.95 h/km during high intensity physical activity and a gradient of 0.49 h/km during low intensity physical activity. The constant 1 refers to one MET. This equation for the expected activity energy expenditure data in METs is illustrated below in FIG. 4A.

The equation for determining the corrected activity energy expenditure data in METs may be determined by referencing the equation of the expected activity energy expenditure data in METs. Correction element 55 or any suitable component of activity monitor 14 may determine to only utilize this equation to correct the raw activity energy expenditure data if the raw activity energy expenditure data is greater than a predetermined threshold value representing the value when the raw activity energy expenditure data begins to become inaccurate as a result of the high intensity physical activity.

This equation for calculating the corrected activity energy expenditure in METs may be:

$$\text{Cor}AEE\_\text{MET}=(\text{Raw}AEE\_\text{MET}-T)*B+F$$

The variable RawAEE_MET used in this equation is the value determined by activity monitor 14 in a previous calculation described above for calculating the raw METs expended by user 12. The constants, T, B, and F, are all associated with determining the corrected activity energy expenditure in METs. The constants, T, B, and F, may be a predetermined value stored in activity monitor 14. These predetermined values associated with the constants may be stored in activity monitor 14 during the manufacture process of activity monitor, by downloading new software for activity monitor, or any other suitable way.

The constant T may be a predetermined value representing a threshold value associated with high intensity physical activity, such that the threshold value is a value from the raw activity energy expended as calculated by activity monitor 14 based on signals from the single uni-axial accelerometer. All raw activity energy expended data above threshold value, T, may be associated with high intensity physical activity, such as running. For example, the threshold value associated with high intensity physical activity, such as running, may be all raw values greater than seven METs. This constant T may be the threshold value used to determine when correction element 55 should be utilized to correct raw activity energy expended data.

The constant B may be a predetermined value representing the gradient of the corrected activity energy expenditure data in METs. For example, B may be the quotient of the gradient G of the expected raw activity energy expenditure data in METs divided by the gradient of the raw activity energy expenditure data in METs. The constant F may be a predetermined value representing the offset value to apply to this equation, such that the offset value results in the corrected activity energy expenditure data in METs to essentially map the expected activity energy expenditure data in METs. The steps for calculating the corrected activity energy expenditure data in METs (CorAEE_MET) are explained in more detail below in FIGS. 4A-4D.

In one embodiment, correction element 55 may determine to utilize the equation for determining the corrected activity energy expenditure data for only the raw activity energy expenditure data associated with high intensity physical activity, such as running. For example, when the MET is used as the physical activity metric, correction element 55 may determine to only utilize the equation for determining the corrected activity energy expenditure data for raw activity energy expenditure data greater than the threshold constant T. The threshold constant T is used as the determinant because this is the threshold value where the uni-axial accelerometer begins to generate inaccurate raw activity energy expended data because of high intensity physical activity. As a result of applying the equation for determining the corrected activity energy expenditure data, activity monitor 14 comprising a single uni-axial accelerometer may be operable to display an accurate activity energy expended data during both low and high intensity physical activity.

In alternative embodiments, other physical activity metrics, such as PAM points, may have their own equations for expected activity energy expended data and corrected activity energy expended data. Correction element 55 may apply the different equations for calculating the corrected activity energy expended data similarly to the MET, such that the equation may comprise a variable of the raw activity energy expended data, such as RawAEE_PAM, and one or more predetermined constants associated with the particular physical activity metric.

Speed element 56 may represent any suitable combination of hardware, software, and/or controlling logic operable to receive the raw activity energy expended data and/or the corrected activity energy expended data. Speed element may use this received data in its speed equation for determining the speed of user 12 during physical activity. Speed equation may calculate speed of user 12 by taking the inverse of the expected activity energy expected equation, such that the energy expended by user 12 is directly related to the velocity of user 12. The relationship between expected activity energy expended data and speed of user 12 is illustrated below in FIG. 4E.

In one embodiment, speed element 56 may determine to use the raw activity energy expended data in the speed equation to determine speed of user 12 during low intensity activity. In one embodiment, speed element 56 may determine to use the corrected activity energy expended data in the speed equation to determine speed of user 12 during high intensity activity. For example, when the MET is used as the physical activity metric, speed element 56 may determine to use the corrected activity energy expended data in the speed equation if the raw activity energy expenditure data is greater than the threshold constant T. If the raw activity energy expenditure data in METs is less than threshold constant T, speed element 56 may determine to use the raw activity energy expended data in the speed equation. As a result, activity monitor 14 comprising a single uni-axial accelerometer may be operable to display an accurate speed of user 12 during both low and high intensity physical activity. Additionally, speed element 56 allows activity monitor to display speed of user without requiring user to input any personal information, such as height or weight.

For example, the equation for calculating the speed of user 12 utilizing the MET as the physical activity metric may be a function of low intensity physical activity, such as walking, and a function of high intensity physical activity, such as running, as published by the American College of Sports Medicine (Ainsworth et al., Compendium of physical activities: An update of activity codes and MET intensities, Med. Sci. Sports. Exerc. 2000, S498-S516). The equation for calculating the speed of user 12 associated with METs expended during low intensity physical activity may be:

$$\text{LowIntensitySpeed}=(\text{Raw}AEE\_\text{MET}-1)/G$$

For the LowIntensitySpeed calculation, the variable RawAEE_MET is the raw activity energy expenditure data calculated previously. The constant G is 0.49 h/km for low intensity physical activity, such as walking, that occurs while the velocity of user 12 is less than eight km/h. The constant 1 refers to one MET.

The equation for calculating the speed of user 12 associated with METs expended during high intensity physical activity may be:

$$\text{HighIntensitySpeed}=(\text{Cor}AEE\_\text{MET}-1)/G$$

For the HighIntensitySpeed calculation, the variable CorAEE_MET is the corrected activity energy expenditure data calculated previously. The constant G is 0.95 h/km for high intensity physical activity, such as running, that occurs while the velocity of user 12 is greater than eight km/h. The constant 1 refers to one MET.

Computer device 16 may include appropriate input devices, output devices, mass storage media, processors, memory, or other components for receiving, processing, storing, and/or communicating information with other components of system 10. As used in this document, the term "computer" is intended to encompass a docking station, personal computer, health station, workstation, network computer, wireless data port, wireless telephone, personal digital assistant (PDA), cellular telephone, game console, one or more processors within these or other devices, or any other suitable processing device. It will be understood that any number of computer devices 16 may be coupled to other computer devices 16 or communication network 18. Computer devices 16 are generally operated by users 12 or coupled with activity monitors 14 to access web portal 40.

In one embodiment, computer device 16 may comprise a browser application, such as an Internet web browser, for example. Browser application may allow user 12 of computer device 16 to navigate through, or "browse," various Internet web sites or web pages. Computer device 16 may also comprise one or more graphics applications, such as a FLASH™ application for example, operable to display various types of data received via communication network 18, such as graphics, video, and streaming data (such as video and/or audio), for example.

In one embodiment, activity monitor 14 may be coupled to computer device 16 such that user 12 can access web portal 40 without intervention from a third party (for example, a webmaster forwarding information) Activity monitor 14 may function as a digital key to web portal 40 so that users instantly access web portal 40 without having to launch an Internet web browser or type in a username or password. The user will be able to instantly interact with web portal 40.

Server 32 is generally operable to provide an interface between users 12 and web portal 40. One or more servers 32 may be web application servers or simple processors operable to allow users 12 to participate with web portal 40 via the communication network 18 using a standard user interface language such as, for example, the HyperText Markup Language (HTML). In some embodiments, one or more servers 32 may be physically distributed such that each server 32, or multiple instances of each server 32, may be located in a different physical location geographically remote from each other. In other embodiments, one or more servers 32 may be combined and/or integral to each other. One or more servers 32 may be implemented using a general-purpose personal computer (PC), a Macintosh, a workstation, a UNIX-based computer, a server computer, or any other suitable processing device.

In one embodiment, server 32 may be operable to configure and/or update all activity monitors 14 of a group of users 12, such that all activity monitors 14 used by a particular business entity are configured and/or updated with the same functionality, such as using the same activity data metrics. For example, business entity may desire to have all activity data displayed with PAM points now instead of METs as was originally installed on activity monitor. This software update to utilize PAM points may include loading a new equation for calculating raw PAM points based on signals from accelerometer, and a new equation utilized by correction element for correcting the raw PAM points to a corrected PAM points value representing the actual energy expended by user.

In one embodiment, server 32 may be operable to provide security and/or authentication of users 12 or other persons or entities attempting to access web portal 40. For example, servers 32 may essentially provide a firewall for entities attempting to access web portal 40. In addition, servers 32 may be operable to translate one or more data protocols used by web portal 40 with one or more protocols used by applications hosted by one or more computer devices 16.

In one embodiment, one or more servers 32 are web application servers operable to communicate dynamically updated information to particular computer devices 16 via communication network 18 including the identity of user 12. For example, one or more servers 32 may communicate updated information on web portal 40 to particular computer devices 16 or activity monitors 14 via communication network 18.

Server 32 may further comprise a memory that may be accessed or otherwise utilized by one or more components of interactive community. The memory may take the form of volatile or non-volatile memory including, without limitation, magnetic media, optical media, random access memory (RAM), read-only memory (ROM), removable media, or any other suitable local or remote memory component. In general, the server memory may store various data including a user's account information, a user's goals, a user's activity data, and a population's activity data.

Databases 34 may be operable to store various data associated with web portal 40, such as information regarding users 12, computer devices 16, and activity monitors 14. Databases 34 may communicate with servers 32 such that servers 32 may store information, retrieve information, and share information with each other. Databases 34 may provide a backup in the case of outages or other failures of various components of web portal. Other architectures and components of servers 32 may be used without departing from the scope of this disclosure.

Web portal 40 may comprise one or more web sites. Web portal may also comprise hardware and software that provide users of the web with the ability to search for information on the web including information in the web portal 40, documents, media, or other resources coupled to the web. The web sites on web portal 40 may include user's websites and informational websites. Web portal 40 provides a central location for users to get together with each other.

In one embodiment, web portal 40 may require user 12 to log in. User 12 may be required to enter a username and password to access personal page. In one embodiment, activity monitor 14 may be associated with a unique id number and web portal 40 may automatically log in user 12 to web portal when user 12 connects activity monitor 14 to computer device 16. Activity monitor 14 may update information stored in database 34 of web portal 40, such as updated activity energy expended data. Web portal 40 may comprise a personal coach page for user 12 comprising personal data of user 12, such as the name, photo, address, city, country, weight, height, age, gender, and weight goal. Logic in web portal 40 may use personal data of user 12 to generate instructions or update goals.

The personal goals of user 12 in terms of a desired activity zone level and a desired weight may be calculated and displayed on a page in web portal 40. Such calculations may be based on the personal data of user 12, such as weight, height, age, and gender, as well as on other personal parameters that can be changed and/or updated on a preferences page and/or on the METs expended of the first week and/or a numerical parameter representing the motivation of user 12. Upon approval of user, the calculated goals are set to be reached at the end of a specified time period, such as six months. During this period, the personal user page may provide information concerning the personal history of user 12 in terms of activity, body weight, and advice comprising suggestions for reaching the personal goals, such as walking a half an hour every day and running five km every day.

In one embodiment, web portal 40 comprises a resource page including links to interesting pages that may help user 12 reach the personal goals, such as a link to a page containing recipes which support a healthy lifestyle, a link to a service providing direct access to an instructor or dietician, and a link containing information on regional activities. If a goal is reached by user 12, the personal page may display a message congratulating user 12 or send an actual congratulations post card to user's address. A special printer associated with web portal may do this automatically.

Figure 2:
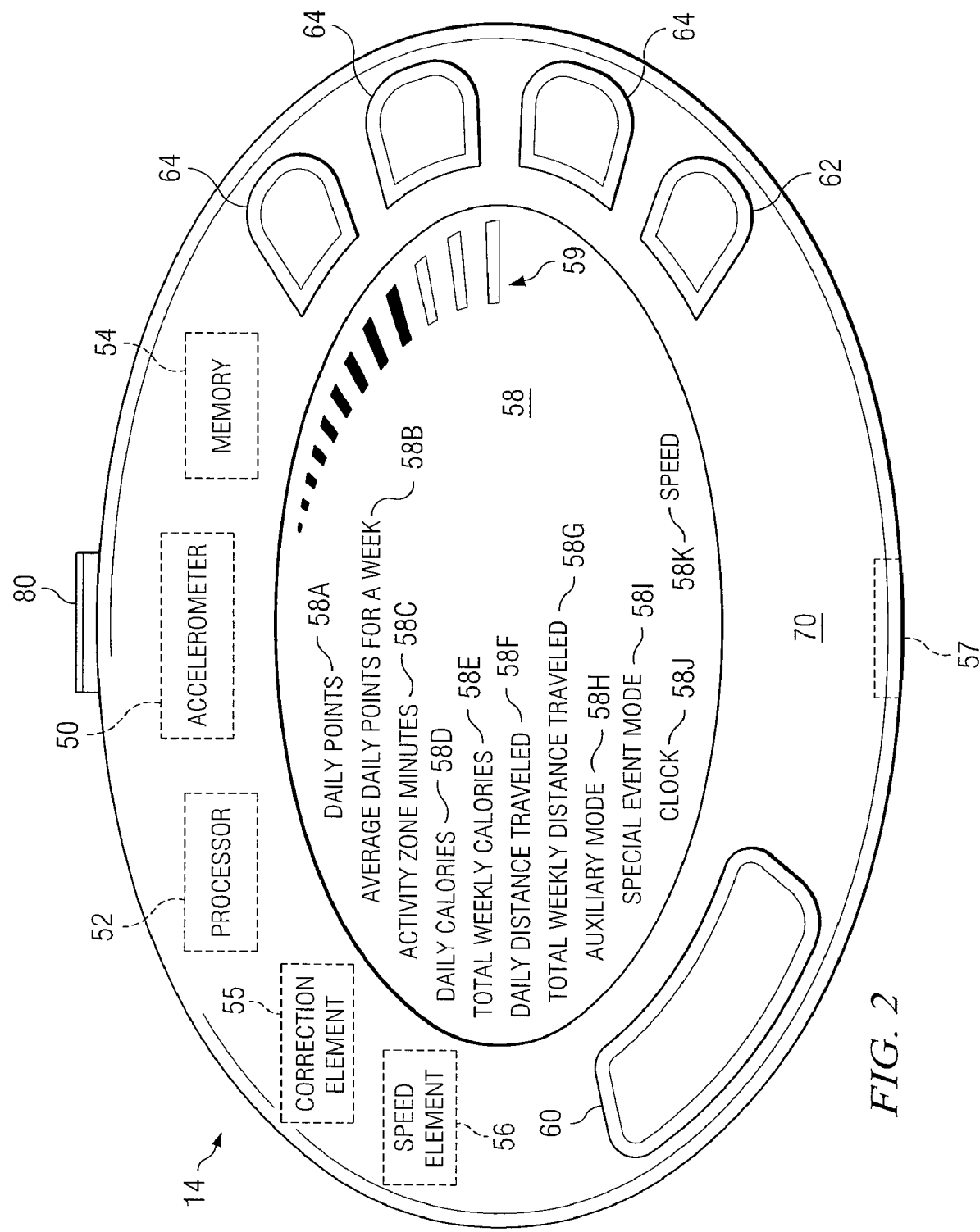
FIG. 2 is a simplified block diagram that illustrates an activity monitor apparatus used in the system in accordance with a particular embodiment of the present invention.

FIG. 2 is a simplified block diagram that illustrates an activity monitor apparatus used in the system in accordance with a particular embodiment of the present invention. Activity monitor 14 includes an accelerometer 50, a processor 52, a memory 54, a correction element 55, a speed element 56, a port 57, a display 58, a mode button 60, a special event button 62, one or more input buttons 64, a skin 70, and a clip 80. Display 58 is operable to display an activity meter 59 and several different modes including daily points 58A, average daily points for a week 58B, activity zone minutes 58C, daily calories 58D, total weekly calories 58E, daily distance traveled 58F, total weekly distance traveled 58G, auxiliary mode 58H, special event mode 58I, a clock 58J, and speed 58K.

Accelerometer 50 is a device that is used to convert an acceleration from gravity or from motion into an electrical signal. The input for accelerometer 50 is generally gravity or motion. Accelerometer 50 may measure acceleration in units of "g's." One "g" is defined as the earth's gravitational pull on an object or a person. For example, 1 g represents the acceleration exerted by the Earth's gravity on an object or person (for example, a cell phone on a desk experiences 1 g of acceleration). The acceleration range experienced by a person when walking is between 0.1-2.0 g. In one embodiment, accelerometer 50 may be a uni-axial sensor that measures up and down movement of user along the vertical axis. Accelerometer 50 may determine the raw activity energy expended data by user 12. Accelerometer 50 is explained in more detail below in FIG. 3.

Processor 52 controls the operation and administration of activity monitor 14 by processing information and signals. Processor 52 includes any suitable hardware, software, or both that operate to control and process signals. Processor 52 may be microprocessors, controllers, or any other suitable computing devices, resources, or combination of hardware, software and/or encoded logic. For example, processor 52 may be used to calculate the raw activity energy expended data by utilizing data from accelerometer 50. Processor 52 may also be used by correction element 55 and speed element 56 to determine the corrected activity energy ended data and the speed of user 12.

Memory 54 may be accessed or otherwise utilized by activity monitor 14. Memory 54 may take the form of volatile or non-volatile memory including, without limitation, magnetic media, optical media, random access memory (RAM), read-only memory (ROM), removable media, or any other suitable local or remote memory component. In general, memory 54 may store various data including data from accelerometer, data from processor, and data from web portal. Memory may also include equations and predetermined constants associated with correction element 55 and speed element 56.

Port 56 may communicate information and signals to one or more computer devices 16 and receive information and signals from one or more computer devices 16. Port 56 may also communicate information and signals to communication network 18 and receive information and signals from communication network 18. Port 56 may represent any connection, real or virtual, including any suitable hardware and/or software that may allow activity monitor 14 to exchange information and signals with communication network 18, one or more computer devices 14, and/or other elements of system 10. For example, port 56 enables activity monitor 14 to receive data from web portal 40. Port 56 further enables activity monitor 14 to transmit data to web portal 40 including all updated activity data. Port may be a serial communication port or a Universal Serial Bus (USB) port.

Display 58 is operable to display one or more images in one or more formats. Images viewed in display 58 may include daily points 58A, average daily points for a week 58B, activity zone minutes 58C, daily calories 58D, total weekly calories 58E, daily distance traveled 58F, total weekly distance traveled 58G, auxiliary mode 58H, special event mode 58I, a clock 58J, speed 58K, and an activity meter 59.

Daily points 58A may be viewed on display 58. Daily points 58A may represent any activity data metric associated with activity energy expended. For example, if activity monitor utilized the MET as the activity data metric, then METs expended for the day may be viewed by user 12. The daily points 58A provide user 12 with a simple and straightforward method to quantify and express the total amount of activity that user 12 achieves over a single day. The average daily points for a week 58B allows user 12 to track how consistent user 12 has been active for the past seven days. Web portal 40 or other literature may indicate the amount of daily points 58A users 12 should strive to accumulate to achieve a healthy lifestyle. By displaying a simple format, such as PAM points or METs, activity monitor 14 engages user 12 to stay active until user 12 has expended enough energy. Correction element 55 allows for activity monitor 14 to calculate and display the accurate amount of activity energy expended data, such as PAM points or METs, even when user 12 is engaged in high intensity physical activity.

Activity zone minutes 58C may be viewed on display 58. Activity zones may display life zone minutes, health zone minutes, and sport zone minutes. The activity zones may also be called light zone minutes, medium zone minutes, and heavy zone minutes as described in FIG. 1 above. Life zone minutes may include very light activity, such as slow walking but not sitting down. Health zone minutes may include walking activity (faster than 4 km/h) or comparable activity consistent with recommendations from the medical community necessary for a beneficial health effect, i.e., such as walking thirty minutes a day most days of the week. Sport zone minutes may include running activity or activity with similar physical intensity. Web portal 40 or other literature may indicate the amount of time user 12 should strive to accumulate in the activity zones to achieve a healthy lifestyle. Displaying activity zone minutes 58C engages user 12 to stay active until user 12 has accumulated enough activity zone minutes 58C in each associated activity zone.

Daily calories expended 58D may be viewed on display 58. Correction element 55 allows for activity monitor 14 to calculate and display the accurate amount of calories expended even when user 12 is engaged in high intensity physical activity. The total weekly calories expended 58E may also be viewed on display 58. Web portal 40 or other literature may indicate the amount of calories user 12 should expend to achieve a healthy lifestyle. Displaying the amount of calories expended engages user 12 to stay active until user 12 has expended enough calories.

Daily distance traveled 58F may be viewed on display 58. Activity monitor 14 may allow user 12 to set the measurement of distance including feet, miles or kilometers, etcetera. Total weekly distance 58G traveled may also be viewed on display 58. Web portal 40 or other literature may indicate the amount of distance users 12 should travel to achieve a healthy lifestyle. Displaying the amount of distance traveled engages user 12 to stay active until user 12 has traveled far enough.

Auxiliary mode 58H may be viewed on display 58. In auxiliary mode 58H, user 12 may manually input numbers into activity monitor 14. For example, a physician may give user 12 a regimen to take three pills a day or eat five vegetables a day. Physician or user 12 may input this information into web portal 40. Web portal 40 may transmit this information to activity monitor 14 such that activity monitor 14 may display this information. Activity monitor 14 may be operable for user 12 to manually input each time user 12 takes a pill or eats a vegetable, such that the auxiliary mode displays the updated information. User 12 may press a button on activity monitor 14 for every pill or vegetable. User 12 may connect activity monitor 14 to web portal 40, such that auxiliary mode 58H information is automatically transmitted to web portal 40. Physician may monitor web portal 40 to make sure user 12 is in compliance of a regimen (for example, user is taking the number of pills per day and eating the number of vegetables per day) Auxiliary mode 58H may enable user 12 to properly track a diet regimen. Users 12 may not remember how many pills that they have taken throughout the day, and auxiliary mode 58H enables users 12 to track their personal regimen. Physicians may also monitor their patients to make sure that patients are compliant with the regimen prescribed for them.

Special event mode 58I may be viewed on display 58. Special event mode 58I enables user 12 to begin special event 58I and to end special event 58I. Additionally, special event mode 58I enables machines, like a treadmill, to begin a special event and to end a special event. For example, a treadmill may send a signal to activity monitor 14 to begin a special event when the treadmill is turned on and to end a special event when the treadmill is turned off. The activity monitor 14 may track the activity data during the special event 58I time period, such that user 12 can monitor activity of specific events. Alternatively, user 12 may manually press a button for special event 58I to begin at the start of a marathon and manually press a button for special event 58I to end when user 12 crosses the finish line. Special event mode 58I may enable users to monitor specific activity events, which engages users 12 to become more active.

Clock 58J may be viewed on display 58. Clock 58J may be the time of day. Clock 58J may also be a stopwatch to monitor the amount of time spent on an activity. Activity meter 59 may be viewed on display 58. Activity meter 59 may comprise one or more bars such that no bars are displayed while user 12 is stationary, and the number of bars displayed will increase as user's current activity level increases.

Speed 58K may be viewed on display 58. Speed may be displayed in any suitable units, such as kilometers per hour, miles per hour, etc. By displaying speed 58K, activity monitor 14 engages user 12 to stay active because user 12 has real-time knowledge of current speed. Speed element 56 allows for activity monitor 14 to calculate and display the accurate speed of user 12 even when user 12 is engaged in high intensity physical activity.

Mode button 60 on activity monitor 14 enables user 12 to toggle through one or more display modes for user 12 to view. For example, user 12 may press mode button 60 to toggle display 58 from daily points to daily calories expended 58D to special event mode 58I, etcetera. Special event button 62 on activity monitor 14 enables user 12 to begin and to end a special event. One or more input buttons 64 on activity monitor 14 enable user 12 to input information like incrementing the counter in auxiliary mode 58H.

Skin 70 encases the outside of activity monitor 14. Skin 70 may be removable and replaced with one or more skins 70. Skin 70 may have different features including a different color, material, and texture. Clip 80 may attach to back of activity monitor 14. Clip 80 enables user 12 to easily attach activity monitor 14 to an article of clothing. For example, clip 80 associated with activity monitor 14 comprising a single uni-axial accelerometer 50 allows accelerometer 50 to properly measure up and down movement of user 12 along the vertical axis. Clip 80 may be removable and replaced with one or more clips 80. Clip 80 may also have different features including a different color, material, and texture.

Figure 3:
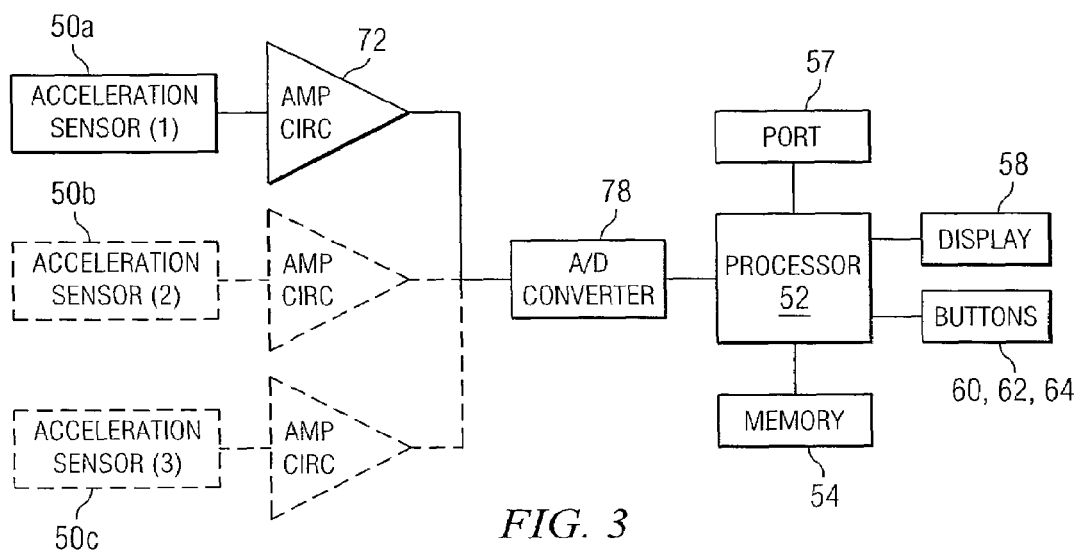
FIG. 3 is a simplified block diagram that illustrates an activity monitor generating signals in response to a user's movement.

FIG. 3 is a simplified block diagram that illustrates an activity monitor generating signals in response to a user's movement. For purposes of teaching and discussion, it is useful to provide some overview as to the way in which the following invention operates. The following foundational information may be viewed as a basis from which the present invention may be properly explained.

The circuitry of activity monitor 14 may comprise a single uni-axial accelerometer 50a, such as a uni-axial piezo-electric accelerometer 50a, which registers up and down body movement of user 12 along the vertical axis. Other types of accelerometer may be employed, such as piezo-resistive accelerometers, capacitive accelerometers, or other types of measuring methods to determine acceleration. The aforementioned clip in FIG. 2 facilitates attachment of activity monitor to user 12, such as attaching to the belt of user 12, in such a way that ensures a substantially horizontal position when user 12 is standing upright. This allows the uni-axial accelerometer 50a to obtain accurate measurements occurring along the vertical axis. In other embodiments, it is possible to use multiple accelerometer sensors 50b, 50c to measure different movements of user 12 along one or more axis.

Accelerometer 50a generates signals associated with movements of user 12. Signals may be filtered using a band-pass filter to make sure that the signals occur in a frequency range typical for human motion, such as from 0.5 to 5 Hz with an amplitude of less than 5 G. Signal may be an analogous signal, such that a voltage fluctuates in a range from 0 mV to 10 mV.

This signal is subsequently amplified by means of amplification circuitry 72 and converted to a digital sequence of numbers by means of an A/D converter 78 with a sample frequency, such as 32 Hz. A dedicated processor 52 calculates the average of the absolute value of the acceleration data over a specified time, such as the last second, last minute, last day or the last week. The average of the absolute value of the acceleration data over a specified time is used to obtain the raw activity energy expended data.

For example, as described above in FIG. 1, the formula for calculating the raw activity energy expended data in METs may be:

$$\text{Raw}AEE\_\text{MET} = (c*|a|)+1$$

To calculate the average value of the MET over a certain period of time, such as a day, the signal may be processed as follows. The signal, which fluctuates within the said range of 0 mV to 10 mV, is amplified by an amplification factor and sampled by the A/D converter 78, which then generates a sample value, such as an integer in a range from 0 to 1024. Subsequently the absolute value is calculated so that the average of the values may represent the variable |a|. The constant c may be a predetermined number, such that the value of c may be determined by comparing the |a| value in METs with the expected value in METs obtained by measuring the actual energy expended by a plurality of subjects.

In one embodiment, activity monitor 14 may utilize a calibration factor to compensate for variations specific to the accelerometer type used. For example, piezo-electric sensor variations are plus or minus five percent. Therefore, a calibration factor for piezo-electric sensors may be in a range from 0.95 to 1.05.

Processor 58 may store the RawAEE_MET in memory. Activity monitor 14 may display RawAEE_MET or it may determine that correction element 55 and/or speed element 56 should process the RawAEE_MET.

Figure 4A:
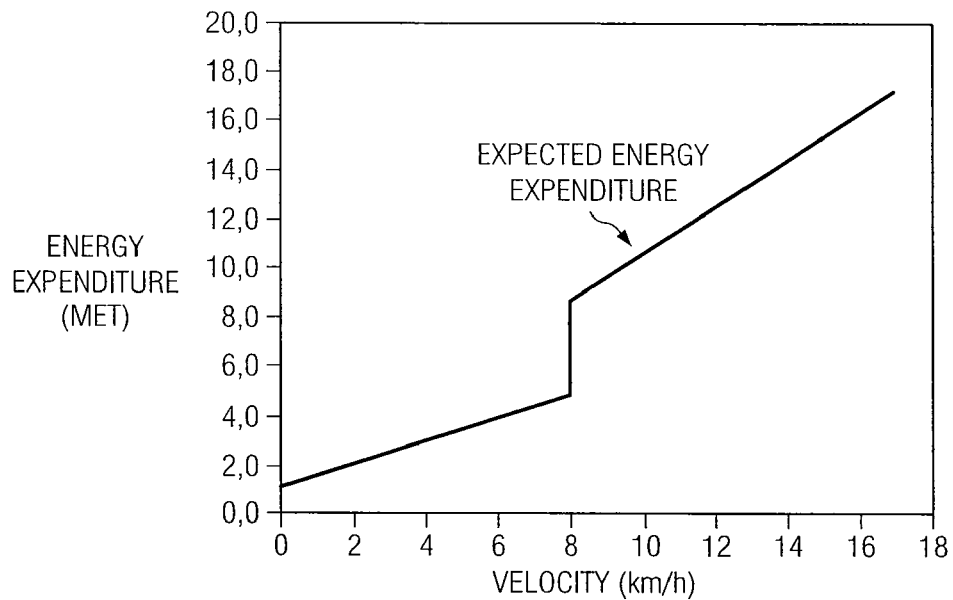
FIG. 4A is a graph illustrating an example equation for calculating the expected activity energy expended data in METs.

FIG. 4A is a graph illustrating an example equation for calculating the expected activity energy expended data in METs. In one embodiment, correction element 55 may utilize an equation to determine the corrected activity energy expenditure data (CorAEE). The equation utilized by correction element 55 may be based on the expected activity energy expenditure data (ExpAEE). The expected activity energy expenditure data for a particular activity data metric may be determined by a formula that expresses a relationship between the actual energy expended during low intensity physical activity, such as walking, and the actual energy expended during high intensity physical activity, such as running.

For example, the equation for calculating the expected activity energy expenditure data using the MET as the physical activity metric may be a function of low intensity physical activity, such as walking, and a function of high intensity physical activity, such as running, as published by the American College of Sports Medicine (Ainsworth et al., Compendium of physical activities: An update of activity codes and MET intensities, Med. Sci. Sports. Exerc. 2000, S498-S516). This equation for calculating the expected activity energy expenditure data in METs may be:

$$\mathrm{Exp}AEE\_MET = (G*v) + 1$$

Figure 4B:
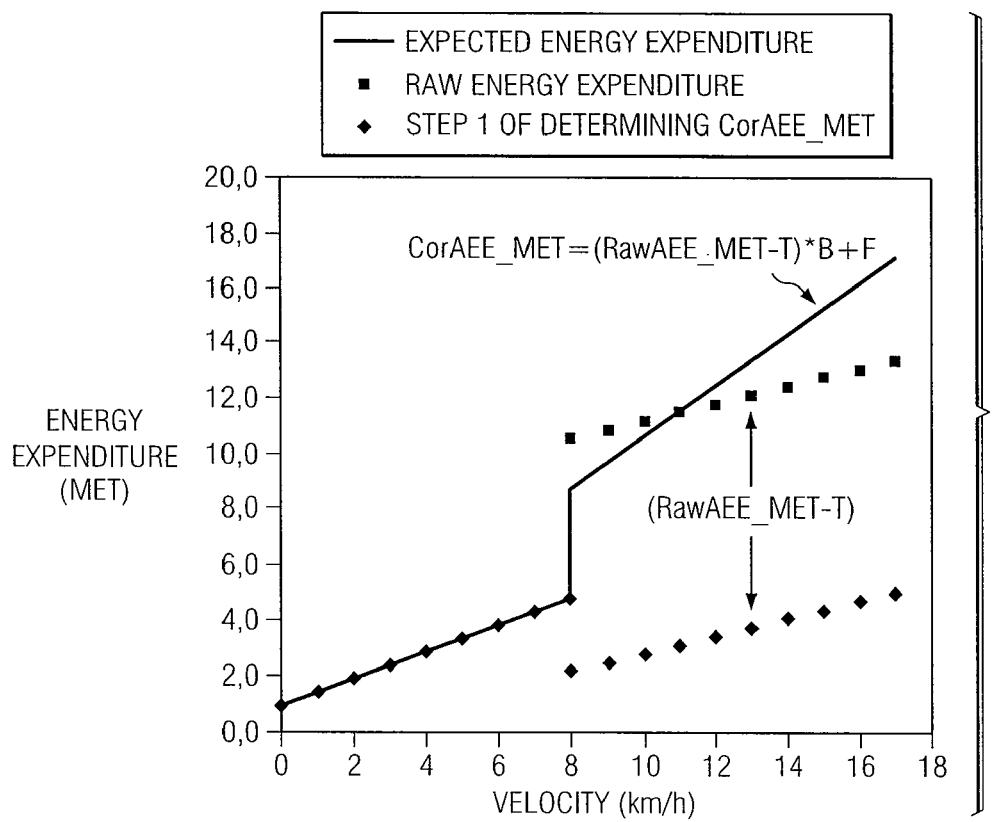
FIG. 4B is a graph illustrating step one of an example equation for calculating the corrected activity energy expended data in METs.

The variable v used to calculate ExpAEE_MET is the velocity of user 12 in terms of km/h. The constant G is 0.49 h/km for low intensity physical activity, such as walking, that occurs while the velocity of user 12 is less than eight km/h. The constant G is 0.95 h/km for high intensity physical activity, such as running, that occurs while the velocity of user 12 is greater than eight km/h. The constant G represents the gradient, such that activity energy expended increases at a gradient of 0.95 h/km during high intensity physical activity and a gradient of 0.49 h/km during low intensity physical activity. The constant 1 refers to one MET. This equation for the expected activity energy expenditure data is illustrated by the graph in FIG. 4A. FIG. 4B is a graph illustrating step one of an example equation for calculating the corrected activity energy expended data in METs. The equation for determining the corrected activity energy expenditure data in METs may be determined by referencing the equation of the expected activity energy expenditure data in METs. This equation for calculating the corrected activity energy expenditure in METs may be:

$$\mathrm{Cor}AEE\_MET = (\mathrm{Raw}AEE\_MET - T)*B + F$$

The variable RawAEE_MET used in this equation is the value determined by activity monitor 14 in a previous calculation described above for calculating the raw METs expended by user 12. The constants, T, B, and F, are all associated with determining the corrected activity energy expenditure in METs. The constants, T, B, and F, may be a predetermined value stored in activity monitor 14. These predetermined values associated with the constants may be stored in activity monitor 14 during the manufacture process of activity monitor, by downloading new software for activity monitor, or any other suitable way.

The constant T may be a predetermined value representing a threshold value associated with high intensity physical activity, such that the threshold value is a value from the raw activity energy expended as calculated by activity monitor 14 based on signals from the single uni-axial accelerometer. All raw activity energy expended data above threshold value, T, may be associated with high intensity physical activity, such as running. For example, the threshold value associated with high intensity physical activity, such as running, may be all raw values greater than five METs. As will be explained later, this constant T may also be used to determine when correction element 55 should be utilized to correct raw activity energy expended data.

As illustrated in the graph of FIG. 4B, the first step of calculating the corrected activity energy expenditure data in METs may involve subtracting the constant T from the variable RawAEE$_{13}$ MET.

Figure 4C:
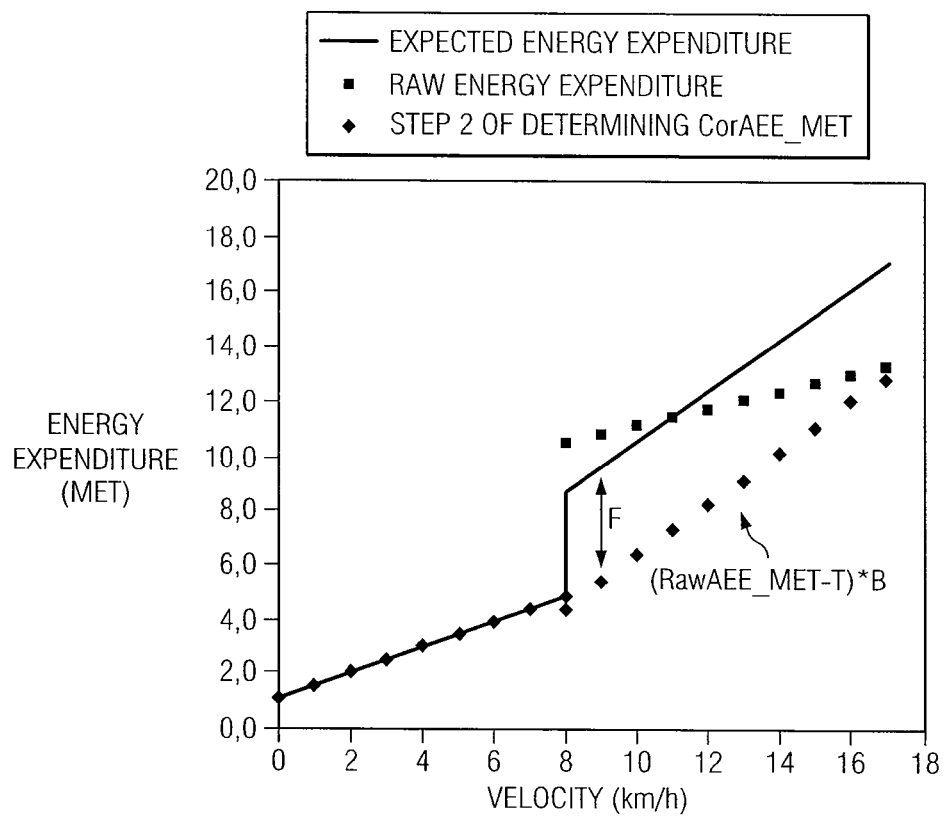
FIG. 4C is a graph illustrating step two of an example equation for calculating the corrected activity energy expended data in METs.

FIG. 4C is a graph illustrating step two of an example equation for calculating the corrected activity energy expended data in METs. The constant B may be a predetermined value representing the gradient of the corrected activity energy expenditure data in METs. For example, B may be the quotient of the gradient G of the expected raw activity energy expenditure data in METs divided by the gradient of the raw activity energy expenditure data in METs. As illustrated in the graph of FIG. 4C, the second step of calculating the corrected activity energy expenditure data in METs may involve multiplying the factor B to the value obtained from subtracting the constant T from the variable RawAEE_MET.

Figure 4D:
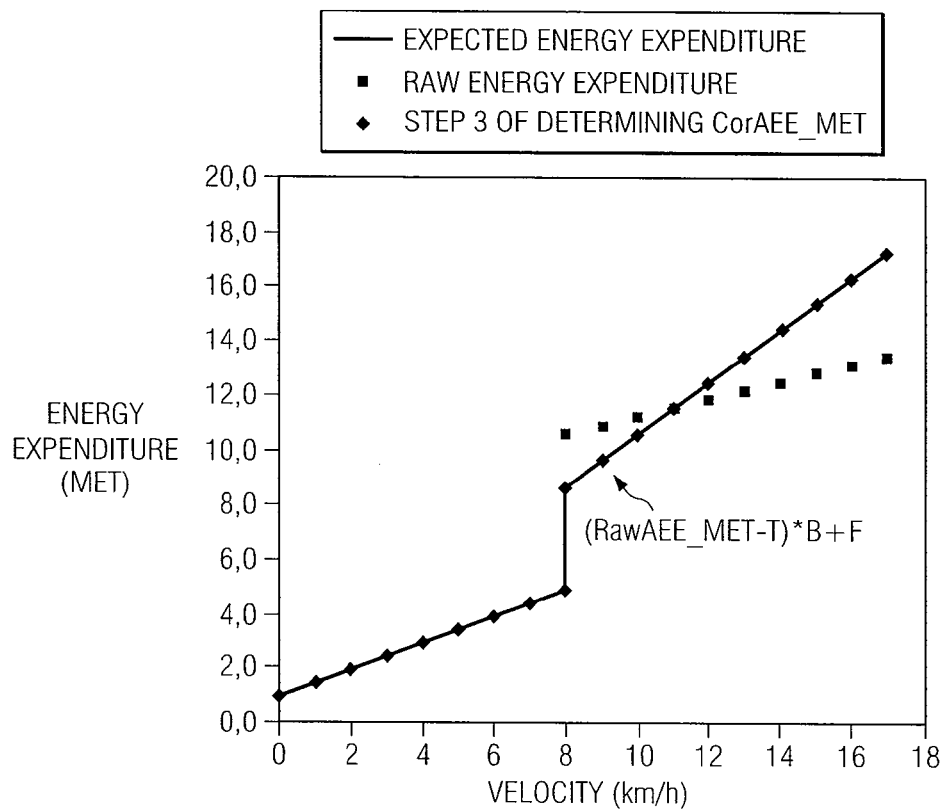
FIG. 4D is a graph illustrating step three of an example equation for calculating the corrected activity energy expended data in METs.

FIG. 4D is a graph illustrating step three of an example equation for calculating the corrected activity energy expended data in METs. The constant F may be a predetermined value representing the offset value to apply to this equation, such that the offset value results in the corrected activity energy expenditure data in METs to essentially map the expected activity energy expenditure data in METs. As illustrated in the graph of FIG. 4D, the third step of calculating the corrected activity energy expenditure data in METs may involve adding the offset, F, to the value obtained by multiplying the factor B to the value obtained from subtracting the constant T from the variable RawAEE_MET.

Figure 4E:
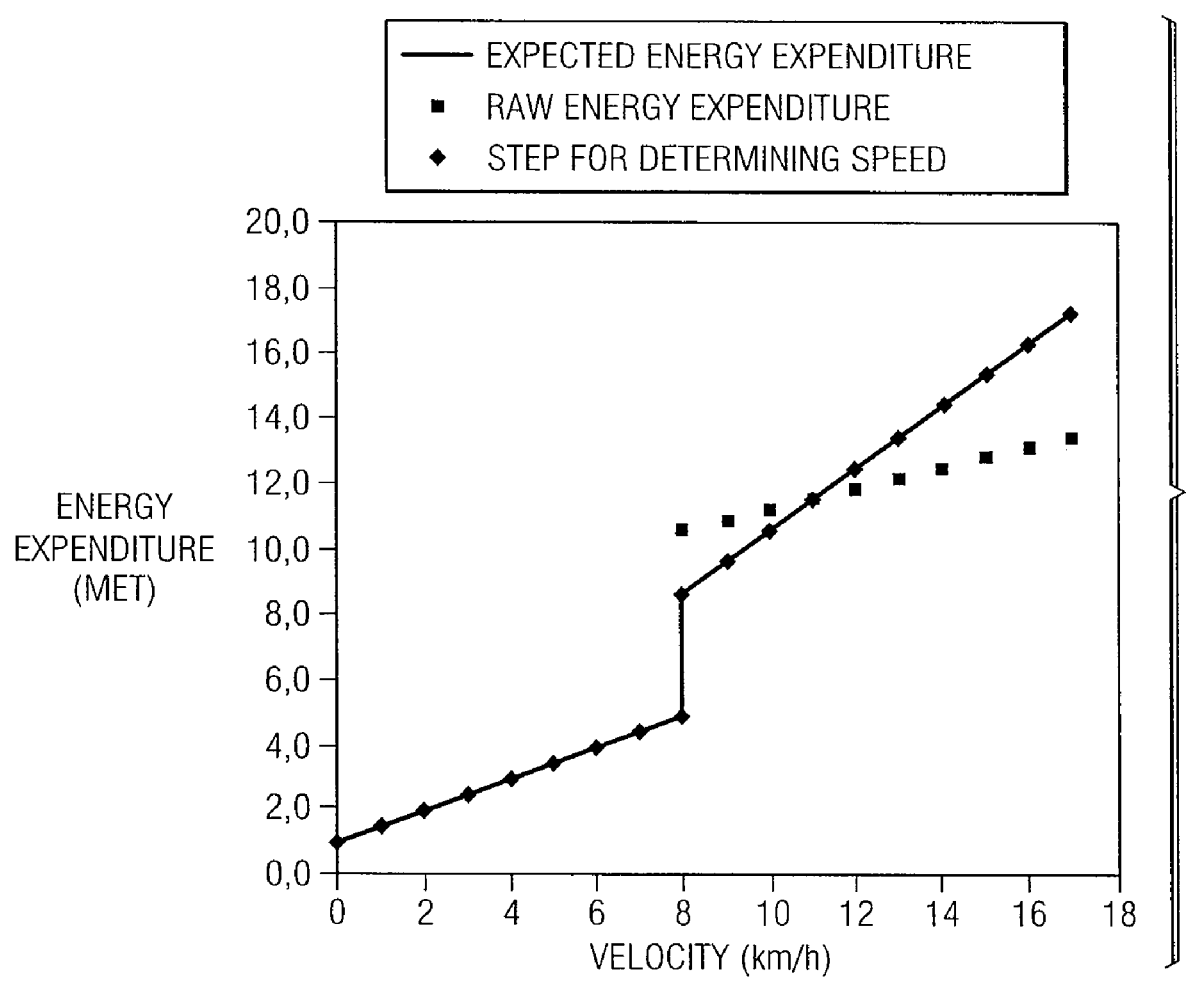
FIG. 4E is a graph illustrating an example equation for calculating the speed of a user based on METs expended.

FIG. 4E is a graph illustrating an example equation for calculating the speed of user based on METs expended. For example, the equation for calculating the speed of user 12 utilizing the MET as the physical activity metric may be a function of low intensity physical activity, such as walking, and a function of high intensity physical activity, such as running, as published by the American College of Sports Medicine (Ainsworth et al., Compendium of physical activities: An update of activity codes and MET intensities, Med. Sci. Sports. Exerc. 2000, S498-S516). The equation for calculating the speed of user 12 associated with METs expended during low intensity physical activity may be:

$$\mathrm{LowIntensitySpeed} = (\mathrm{Raw}AEE\_MET - 1)/G$$

For the LowIntensitySpeed calculation, the variable RawAEE_MET is the raw activity energy expenditure data calculated previously. The constant G is 0.49 h/km for low intensity physical activity, such as walking, that occurs while the velocity of user 12 is less than eight km/h. The constant 1 refers to one MET.

The equation for calculating the speed of user 12 associated with METs expended during high intensity physical activity may be:

HighIntensitySpeed=(Cor$AEE$_MET−1)/G

For the HighIntensitySpeed calculation, the variable CorAEE_MET is the corrected activity energy expenditure data calculated previously. The constant G is 0.95 h/km for high intensity physical activity, such as running, that occurs while the velocity of user 12 is greater than eight km/h. The constant 1 refers to one MET.

Figure 5:
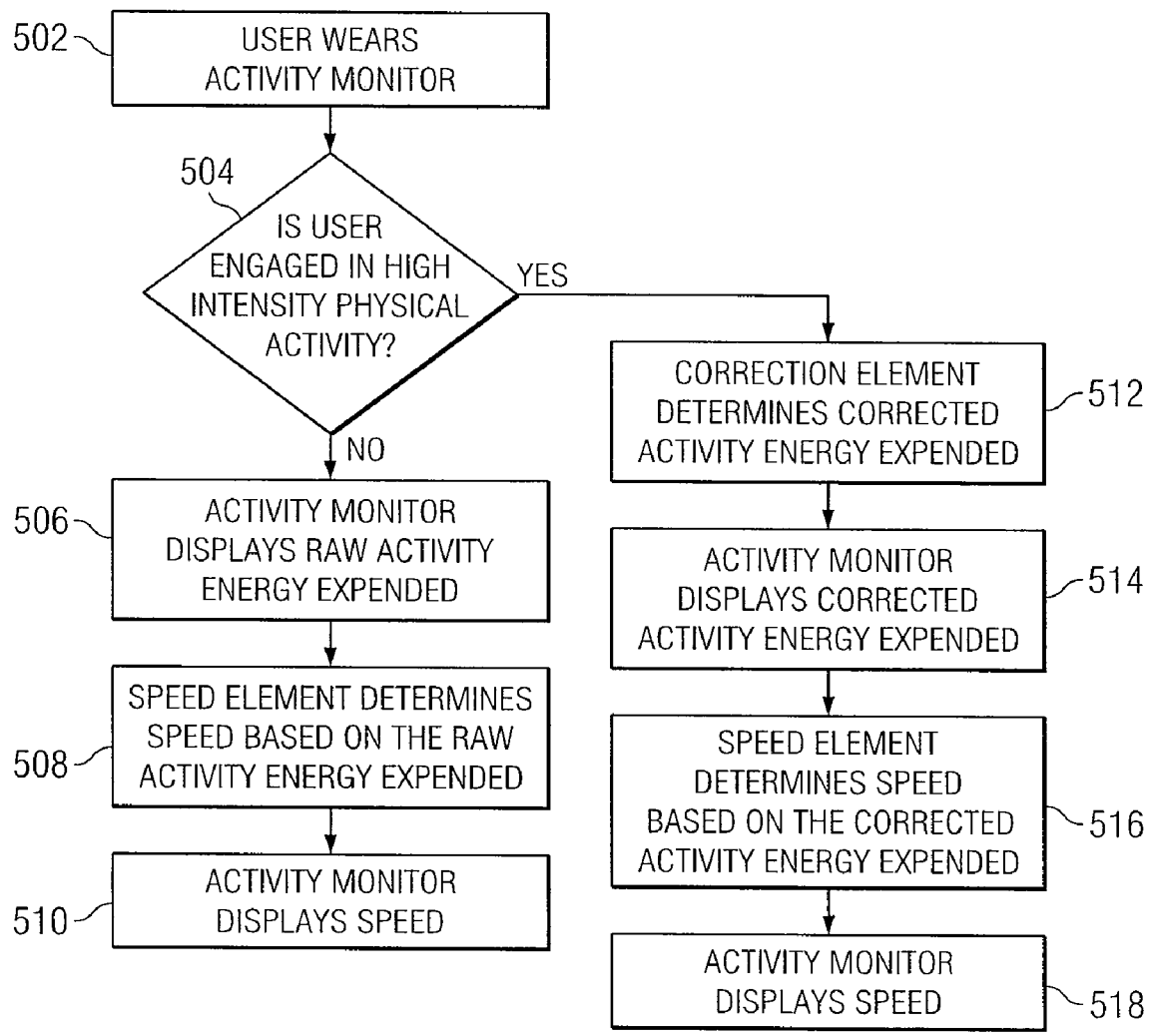
FIG. 5 is a flowchart that illustrates an example method of correction element and speed element in accordance with an embodiment of the present invention.

FIG. 5 is a flowchart that illustrates an example method of correction element 55 and speed element 56 in accordance with an embodiment of the present invention.

The flowchart begins at step 502, when user wears activity monitor. Activity monitor may comprise a single uni-axial accelerometer. Activity monitor may be preprogrammed with equations and the associated predetermined constants of the equations for calculating the raw activity energy expenditure data in METs, the corrected activity energy expenditure data in METs, and the speed of user based on METs expended by user. As a result, user may wear a new activity monitor and view the actual energy expended by user and the speed of user, such that user never has to input any personal information for these calculations.

At step 504, activity monitor determines if user is engaged in low or high intensity physical activity. The raw activity energy expenditure data in METs can be compared to the predetermined threshold constant, T. The predetermined threshold constant, T, may represent the value where raw activity energy expenditure data deviates from the expected activity energy expenditure data as a result of high intensity physical activity. If the raw activity energy expenditure data in METs is equal to or greater than the predetermined threshold constant, T, then user is engaged in high intensity physical activity and activity monitor moves to step 512 to utilize correction element. Otherwise, if the raw activity energy expenditure data in METs is less than the predetermined threshold constant, T, then user is engaged in low intensity physical activity and activity monitor moves to step 506.

At step 506, activity monitor has determined user is engaged in low intensity physical activity. When engaged in low intensity physical activity, the single uni-axial accelerometer generates accurate values for raw activity energy expenditure data. Therefore, activity monitor displays the raw activity energy expenditure data in METs to user.

At step 508, speed element determines speed of user based on the raw activity energy expended. At step 510, activity monitor displays speed to user.

At step 512, activity monitor has determined user is engaged in high intensity physical activity. When engaged in high intensity physical activity, the single uni-axial accelerometer generates inaccurate values for raw activity energy expenditure data. Therefore, activity monitor communicated the raw activity energy expenditure data in METs to correction element. Correction element utilizes a predetermined equation associated with METs to calculate a corrected activity energy expenditure data in METs, which represents the actual METs expended by user. At step 514, activity monitor displays the corrected activity energy expenditure data in METs to user.

At step 516, speed element determines speed of user based on the corrected activity energy expended. At step 518, activity monitor displays speed to user.

It is important to note that the stages and steps described above illustrate only some of the possible scenarios that may be executed by, or within, the present system. Some of these stages and/or steps may be deleted or removed where appropriate, or these stages and/or steps may be modified, enhanced, or changed considerably without departing from the scope of the present invention. In addition, a number of these operations have been described as being executed concurrently with, or in parallel to, one or more additional operations. However, the timing of these operations may be altered. The preceding example flows have been offered for purposes of teaching and discussion. Substantial flexibility is provided by the tendered architecture in that any suitable arrangements, chronologies, configurations, and timing mechanisms may be provided without departing from the broad scope of the present invention. Accordingly, communications capabilities, data processing features and elements, suitable infrastructure, and any other appropriate software, hardware, or data storage objects may be included within system 10 to effectuate the tasks and operations of the elements and activities associated with executing compatibility functions.

Although the present invention has been described in detail with reference to particular embodiments, it should be understood that various other changes, substitutions, and alterations may be made hereto without departing from the spirit and scope of the present invention. The illustrated network architecture of FIG. 1 has only been offered for purposes of example and teaching. Suitable alternatives and substitutions are envisioned and contemplated by the present invention: such alternatives and substitutions being clearly within the broad scope of system 10. For example, the use of the LAN could easily be replaced by a virtual private network (VPN), a metropolitan area network (MAN), a wide area network (WAN), a wireless LAN (WLAN), or any other element that facilitates data propagation. Using analogous reasoning, the computer device illustrated by FIG. 1 may be supplanted by docking stations, health stations, gaming consoles, or any other suitable devices that are conducive to network communications. Furthermore, the activity monitor is not confined to displaying only the modes shown in FIG. 2.

Although the present invention has been described with several embodiments, a myriad of changes, variations, alterations, transformations, and modifications may be suggested to one skilled in the art, and it is intended that the present invention encompass such changes, variations, alterations, transformations, and modifications as falling within the scope of the appended claims.

What is claimed is:

1. A method, comprising:
    calculating, by an activity monitor comprising one accelerometer, a raw activity energy expenditure data based on movement by a user;
    determining if the raw activity energy expenditure data is associated with a high intensity physical activity, wherein the high intensity physical activity causes the raw activity energy expenditure data to differ from an expected activity energy expenditure data;
    calculating, through a processor, a corrected activity energy expenditure data, if the raw activity energy expenditure data is associated with the high intensity physical activity, based on the raw activity energy expenditure data; and storing the corrected activity energy expenditure data, wherein the raw activity energy expenditure data in metabolic equivalents is calculated by $(c*|a|)+1$, wherein c is a predetermined value stored in the activity monitor, wherein $|a|$ is the absolute value of the acceleration determined by the activity monitor based on signals generated by the one accelerometer, and wherein 1 is one metabolic equivalent (MET).

2. The method of claim 1, further comprising displaying the corrected activity energy expenditure.

3. The method of claim 1, further comprising:

determining a speed of the user based on the raw activity energy expenditure data if the raw activity energy expenditure data is not associated with the high intensity physical activity, or based on the corrected activity energy expenditure data if the raw activity energy expenditure data is associated with the high intensity physical activity; and displaying the speed of the user.

4. The method of claim 3, wherein the speed of the user is determined by $(RawAEE\_MET-1)/0.49$ kilometer/hours (km/h) if the speed of the user is based on the raw activity energy expenditure data, or by $(CorAEE\_MET-1)/0.95$ km/h if the speed of the user is based on the corrected activity energy expenditure data, wherein the RawAEE_MET is the raw activity energy expenditure data in metabolic equivalents (METs), wherein the CorAEE_MET is the corrected activity energy expenditure data in METs, wherein 1 is one MET.

5. The method of claim 1, wherein the determining if the raw activity energy expenditure data is associated with the high intensity physical activity comprises determining if the raw activity energy expenditure data is greater than a predetermined threshold value.

6. The method of claim 1, wherein the corrected activity energy expenditure data in metabolic equivalents is calculated by $(RawAEE\_MET-T)*B+F$, wherein RawAEE_MET is the raw activity energy expenditure data, wherein T is a predetermined threshold value associated with the high intensity physical activity, wherein B is a predetermined gradient value, wherein F is a predetermined offset value.

7. The method of claim 1, wherein the corrected activity energy expenditure data comprises energy expended by the user in directions other than direction of the movement measured by the accelerometer.

8. The method of claim 1, wherein the one accelerometer is a uni-axial piezo-electric accelerometer.

9. The method of claim 1, wherein the expected activity energy expenditure data in metabolic equivalents is determined by $(G*v)+1$, wherein G is a predetermined gradient value of 0.95 h/km during the high intensity physical activity and 0.49 h/km for low intensity physical activity, wherein v is a velocity of the user, 1 is one MET.

10. An apparatus, comprising:
one accelerometer;
a display;
a processor operable to:
calculate a raw activity energy expenditure data based on movement by a user;
determine if the raw activity energy expenditure data is associated with a high intensity physical activity, wherein the high intensity physical activity causes the raw activity energy expenditure data to differ from an expected activity energy expenditure data; and
a correction element operable to:
calculate a corrected activity energy expenditure data, if the raw activity energy expenditure data is associated with the high intensity physical activity, based on the raw activity energy expenditure data, wherein the raw activity energy expenditure data in metabolic equivalents is calculated by $(c*|a|)+1$, wherein c is a predetermined value stored in the activity monitor, wherein $|a|$ is the absolute value of the acceleration determined by the activity monitor based on signals generated by the one accelerometer, and wherein 1 is one metabolic equivalent (MET).

11. The apparatus of claim 10, the processor further operable to display the corrected activity energy expenditure.

12. The apparatus of claim 10, further comprising a speed element operable to:

determine a speed of the user based on the raw activity energy expenditure data if the raw activity energy expenditure data is not associated with the high intensity physical activity, or based on the corrected activity energy expenditure data if the raw activity energy expenditure data is associated with the high intensity physical activity; and display the speed of the user.

13. The apparatus of claim 12, wherein the speed of the user is determined by $(RawAEE\_MET-1)/0.49$ km/h if the speed of the user is based on the raw activity energy expenditure data, or by $(CorAEE\_MET-1)/0.95$ km/h if the speed of the user is based on the corrected activity energy expenditure data, wherein the RawAEE_MET is the raw activity energy expenditure data in metabolic equivalents, wherein the CorAEE_MET is the corrected activity energy expenditure data in metabolic equivalents, wherein 1 is one MET.

14. The apparatus of claim 10, wherein the determining if the raw activity energy expenditure data is associated with the high intensity physical activity comprises determining if the raw activity energy expenditure data is greater than a predetermined threshold value.

15. The apparatus of claim 10, wherein the corrected activity energy expenditure data in metabolic equivalents is calculated by $(RawAEE\_MET-T)*B+F$, wherein RawAEE_MET is the raw activity energy expenditure data, wherein T is a predetermined threshold value associated with the high intensity physical activity, wherein B is a predetermined gradient value, wherein F is a predetermined offset value.

16. The apparatus of claim 10, wherein the corrected activity energy expenditure data comprises energy expended by the user in directions other than direction of the movement measured by the accelerometer.

17. The apparatus of claim 10, wherein the one accelerometer is a uni-axial piezo-electric accelerometer.

18. The apparatus of claim 10, wherein the expected activity energy expenditure data in metabolic equivalents is determined by $(G*v)+1$, wherein G is a predetermined gradient value of 0.95 h/km during the high intensity physical activity and 0.49 h/km for low intensity physical activity, wherein v is a velocity of the user, 1 is one MET.

19. Logic encoded in computer-readable media, the logic including code such that when executed on a processor; is configured to:

calculate a raw activity energy expenditure data based on movement by a user, the movement measured by one accelerometer;

determine if the raw activity energy expenditure data is associated with a high intensity physical activity, wherein the high intensity physical activity causes the raw activity energy expenditure data to differ from an expected activity energy expenditure data;

calculate a corrected activity energy expenditure data, if the raw activity energy expenditure data is associated with the high intensity physical activity, based on the raw activity energy expenditure data; and store the corrected activity energy expenditure data, wherein the raw activity energy expenditure data in metabolic equivalents is calculated by (c*|a|)+1, wherein c is a predetermined value stored in the activity monitor, wherein |a| is the absolute value of the acceleration determined by the activity monitor based on signals generated by the one accelerometer, and wherein 1 is one metabolic equivalent (MET).

20. The code of claim 19, wherein the logic is further operable to display the corrected activity energy expenditure.

21. The code of claim 19, wherein the logic is further operable to:

determine a speed of the user based on the raw activity energy expenditure data if the raw activity energy expenditure data is not associated with the high intensity physical activity, or based on the corrected activity energy expenditure data if the raw activity energy expenditure data is associated with the high intensity physical activity; and display the speed of the user.

22. The code of claim 21, wherein the speed of the user is determined by (RawAEE_MET−1)/0.49 km/h if the speed of the user is based on the raw activity energy expenditure data, or by (CorAEE_MET−1)/0.95 km/h if the speed of the user is based on the corrected activity energy expenditure data, wherein the RawAEE_MET is the raw activity energy expenditure data in metabolic equivalents, wherein the CorAEE_MET is the corrected activity energy expenditure data in metabolic equivalents, wherein 1 is one MET.

23. The code of claim 19, wherein the determining if the raw activity energy expenditure data is associated with the high intensity physical activity comprises determining if the raw activity energy expenditure data is greater than a predetermined threshold value.

24. The code of claim 19, wherein the corrected activity energy expenditure data in metabolic equivalents is calculated by (RawAEE_MET−T)*B+F, wherein RawAEE_MET is the raw activity energy expenditure data, wherein T is a predetermined threshold value associated with the high intensity physical activity, wherein B is a predetermined gradient value, wherein F is a predetermined offset value.

25. The code of claim 19, wherein the corrected activity energy expenditure data comprises energy expended by the user in directions other than direction of the movement measured by the accelerometer.

26. The code of claim 19, wherein the one accelerometer is a uni-axial piezo-electric accelerometer.

27. The code of claim 19, wherein the expected activity energy expenditure data in metabolic equivalents is determined by (G*v)+1, wherein G is a predetermined gradient value of 0.95 h/km during the high intensity physical activity and 0.49 h/km for low intensity physical activity, wherein v is a velocity of the user, 1 is one MET.

* * * * *